United States Patent
Mannino et al.

(10) Patent No.: US 11,389,407 B2
(45) Date of Patent: Jul. 19, 2022

(54) COCHLEATES AND METHODS OF USING THE SAME TO ENHANCE TISSUE PENETRATION OF PHARMACOLOGICALLY ACTIVE AGENT

(71) Applicant: Matinas BioPharma Nanotechnologies, Inc., Bedminster, NJ (US)

(72) Inventors: Raphael J. Mannino, Glen Gardner, NJ (US); Ruying Lu, New Providence, NJ (US)

(73) Assignee: MATINAS BIOPHARMA NANOTECHNOLOGIES, INC., Bedminster, NJ (US)

( * ) Notice: Subject to any disclaimer, the term of this patent is extended or adjusted under 35 U.S.C. 154(b) by 77 days.

(21) Appl. No.: 15/554,921

(22) PCT Filed: Mar. 3, 2016

(86) PCT No.: PCT/US2016/020722
§ 371 (c)(1),
(2) Date: Aug. 31, 2017

(87) PCT Pub. No.: WO2016/141203
PCT Pub. Date: Sep. 9, 2016

(65) Prior Publication Data
US 2018/0042849 A1 Feb. 15, 2018

Related U.S. Application Data

(60) Provisional application No. 62/264,164, filed on Dec. 7, 2015, provisional application No. 62/247,641, filed on Oct. 28, 2015, provisional application No. 62/239,675, filed on Oct. 9, 2015, provisional application No. 62/163,212, filed on May 18, 2015, provisional application No. 62/162,425, filed on May 15, 2015, provisional application No. 62/127,799, filed on Mar. 3, 2015.

(51) Int. Cl.

| | |
|---|---|
| *A61K 31/7048* | (2006.01) |
| *A61K 9/127* | (2006.01) |
| *A61K 31/122* | (2006.01) |
| *A61K 31/7036* | (2006.01) |
| *C12N 15/113* | (2010.01) |

(52) U.S. Cl.
CPC .......... *A61K 9/1274* (2013.01); *A61K 31/122* (2013.01); *A61K 31/7036* (2013.01); *A61K 31/7048* (2013.01); *C12N 15/113* (2013.01); *C12N 2310/14* (2013.01); *C12N 2310/3515* (2013.01); *C12N 2320/32* (2013.01)

(58) Field of Classification Search
CPC ................ A61K 9/1274; A61K 31/122; A61K 31/7036; A61K 31/7048; A61K 9/0053; A61K 45/06; C12N 15/113; C12N 2310/14; C12N 2310/3515; C12N 2320/32; A61P 43/00; A61P 37/02; A61P 3/06; A61P 35/00; A61P 33/10; A61P 33/02; A61P 31/12; A61P 31/10; A61P 31/04; A61P 3/02; A61P 25/28
See application file for complete search history.

(56) References Cited

U.S. PATENT DOCUMENTS

| | | |
|---|---|---|
| 4,871,488 A | 10/1989 | Mannino et al. |
| 6,153,217 A | 11/2000 | Jin et al. |
| 8,642,073 B2 | 2/2014 | Mannino et al. |
| 2005/0008686 A1 | 1/2005 | Mannino et al. |
| 2005/0013854 A1 | 1/2005 | Mannino et al. |
| 2012/0178793 A1 | 7/2012 | Mannino et al. |
| 2014/0186430 A1 | 7/2014 | Gould-Fogerite et al. |

FOREIGN PATENT DOCUMENTS

| | | | |
|---|---|---|---|
| WO | 95/09648 A1 | 4/1995 | |
| WO | 2004/012709 A1 | 2/2004 | |
| WO | 2012/151517 A1 | 8/2012 | |
| WO | WO-2013085152 A1 * | 6/2013 | ........... A61K 31/545 |
| WO | 2014/022414 A1 | 2/2014 | |
| WO | 2016/172595 A1 | 10/2016 | |
| WO | 2016/205654 A1 | 12/2016 | |

OTHER PUBLICATIONS

Kim et al. (J. Controlled Release (2006) 116(2), pp. 123-129). (Year: 2006).*
Marques-Gallego et al. (Biomed. Res. Int. (2014) ID 129548;pp. 1-12). (Year: 2014).*
Extended European Search Report dated Jul. 20, 2018 from European Application No. 16759508.1, 9 pages.
International Search Report dated May 12, 2016 from International Application No. PCT/US2016/020722, 9 pages.
Chinese Office Action dated Jan. 3, 2020 from Chinese Patent Application No. 201680026006.3, 24 pages including English Translation.

(Continued)

*Primary Examiner* — J. E. Angell
(74) *Attorney, Agent, or Firm* — MH2 Technology Law Group, LLP

(57) ABSTRACT

A cochleate composition is disclosed. Following oral administration of the cochleate composition, the pharmacologically active agent is found at higher concentrations in the tissue relative to plasma. Oral administration of these cochleate compositions also preferentially targets infected or inflamed tissue as compared to tissue in a healthy subject. The cochleate composition contains a size-regulating agent that reduces cochleate particle size, such as a lipid-anchored polynucleotide, a lipid-anchored sugar, a lipid-anchored polypeptide, or a bile salt (such as oxycholate or deoxycholate). Also disclosed are methods of treatment using the cochleate composition and methods of increasing the concentration of a pharmacologically active agent in an infected tissue relative to the concentration of the pharmacologically active agent in the plasma or the tissue of a healthy subject.

17 Claims, 12 Drawing Sheets
Specification includes a Sequence Listing.

(56) References Cited

OTHER PUBLICATIONS

Cheng et al., "Drug tissue distribution after oral delivery of amphotericin B cochleate and amphotericin B micellar solution in mice", Academic Journal of Second Military Medical University, vol. 35, No. 3, pp. 344-355 (See p. 9 (paragraph 2 and p. 10, paragraphs 1-2) of the translation of Chinese Office Action dated Jan. 3, 2020 for a concise explanation of the relevance of this document, which is referred to as D3 in the Office Action).

* cited by examiner

EGFP Pal+S
  ACCCUGAAGUUCAUCUGCACC-Cy3-S18-Palmitate
ACUGGGACUUCAAGUAGACGU

EGFP Pal
  ACCCUGAAGUUCAUCUGCACC-Cy3-Palmitate
ACUGGGACUUCAAGUAGACGU

EGFP Chol+S
  ACCCUGAAGUUCAUCUGCACC-Cy3-S18-Cholesterol
ACUGGGACUUCAAGUAGACGU

EGFP Chol
  ACCCUGAAGUUCAUCUGCACC-Cy3-Cholesterol
ACUGGGACUUCAAGUAGACGU

EGFP VE+S
VitE-S18-Cy3-ACCCUGAAGUUCAUCUGCACC
         ACUGGGACUUCAAGUAGACGU

EGFP VE
VitE-Cy3-ACCCUGAAGUUCAUCUGCACC
       ACUGGGACUUCAAGUAGACGU

EGFP VEL+S
VitEL-S18-Cy3-ACCCUGAAGUUCAUCUGCACC
           ACUGGGACUUCAAGUAGACGU
EGFP VEL
VitEL-Cy3-ACCCUGAAGUUCAUCUGCACC
        ACUGGGACUUCAAGUAGACGU

FIG. 3

SEQUENCE LISTING

<160> NUMBER OF SEQ ID NOS: 2

<210> SEQ ID NO 1
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1
acccugaagu ucaucugcac c                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
acugggacuu caaguagacg u                                              21
```

COCHLEATES AND METHODS OF USING THE SAME TO ENHANCE TISSUE PENETRATION OF PHARMACOLOGICALLY ACTIVE AGENT

CROSS REFERENCE TO RELATED APPLICATIONS

This application is a U.S. National Phase application of PCT/US2016/020722 filed 3 Mar. 2016, which claims the benefit of, and relies on the filing date of, U.S. provisional patent application No. 62/127,799, filed 3 Mar. 2015; U.S. provisional patent application No. 62/162,425, filed 15 Mar. 2015; U.S. provisional patent application No. 62/163,212, filed 18 May 2015; U.S. provisional patent application No. 62/239,675, filed 9 Oct. 2015; U.S. provisional patent application No. 62/247,641, filed 28 Oct. 2015; and U.S. provisional patent application No. 62/264,164, filed 7 Dec. 2015; the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Mar. 3, 2016, is named 0200.0002-PCT_SL.txt and is 993 bytes in size.

FIELD

This application relates generally to cochleates and methods of administering the same to rapidly deliver a pharmacologically active agent to a targeted tissue.

BACKGROUND

Much of modern pharmacology is based on the absorption of therapeutic agents in the upper part of the intestine, directly into the blood stream leading to first pass liver metabolism. Such first pass metabolism may remove or alter much of the pharmacologic agent administered, thus diminishing the therapeutic effect by reducing the useful dose or by producing metabolites which may cause adverse effects.

Many pharmacologic agents absorbed into the blood stream, are ultimately targeted at tissues elsewhere in the body. Often, the absorption into the blood stream is a method to disperse pharmacologic agents through the body and allow diffusion into the target tissues. This approach may work very well for certain therapeutic applications, but often results in inefficiencies and adverse effects. For instance, many anti-infective agents must reach significant blood levels in order to ultimately penetrate target organs (such as lungs, nasal cavities, or the bladder wall). At the same time, ingestion of pharmacological agents may cause significant side effects in non-targeted tissues, such as the killing of intestinal flora by antibiotics, nausea, vomiting, diarrhea, liver toxicity (from first pass or later metabolization), kidney toxicity (from toxic medications or their metabolites circulating in the blood) or the ulceration of stomach and intestines by non-steroidal anti-inflammatory drugs (NSAIDs).

As a result, the distribution of pharmacological agents via gastro-intestinal absorption into the bloodstream or by injection/infusion typically results in higher blood/serum/plasma levels of the medication versus tissue and organ levels. Also, it often takes significant time for the pharmacological agent to penetrate tissues and organs up to pharmacologically relevant levels.

SUMMARY

The present disclosure provides a cochleate composition, the composition comprising a plurality of cochleates comprising at least one phospholipid (preferably at least one negatively charged phospholipid), a multivalent cation (preferably a divalent metal cation, such as calcium, zinc, magnesium, and barium), a pharmacologically active agent, and a size-regulating agent selected from the group consisting of a lipid-anchored polynucleotide, a lipid-anchored sugar, a lipid-anchored polypeptide, or a bile salt (such as oxycholate or deoxycholate).

In certain embodiments, the mean particle size of the plurality of cochleates is less than 10 microns or alternatively less than 1 micron. In certain embodiments, the mean particle size of the plurality of cochleates is 2-10 times smaller, or alternatively 2-3 times smaller than the mean particle size of cochleates made without the size-regulating agent.

In another aspect, the present disclosure provides a cochleate composition, the composition comprising a plurality of cochleates comprising at least one phospholipid (preferably at least one negatively charged phospholipid), a multivalent cation (preferably a divalent metal cation, such as calcium, zinc, magnesium, and barium), and a pharmacologically active agent, wherein administration of the cochleate composition (preferably oral administration) to a mammal with an infected or inflamed tissue results in higher levels of the pharmacologically active agent in the infected or inflamed tissue relative to levels of the pharmacologically active agent in the plasma.

Also provided is a cochleate composition, the composition comprising a plurality of cochleates comprising at least one at least one phospholipid (preferably at least one negatively charged phospholipid), a multivalent cation (preferably a divalent metal cation, such as calcium, zinc, magnesium, and barium), and a pharmacologically active agent, wherein the tissue levels of the pharmacologically active agent in an infected or an inflamed tissue following administration (preferably oral administration) to a subject is at least 1.5 times higher than the tissue levels of the pharmacologically active agent at 24 hours following administration (preferably oral) to a healthy subject.

Another aspect is directed to a method of treating a subject in need thereof, the method comprising administering a cochleate composition as described herein to the subject.

Yet another aspect is directed to a method of increasing the concentration of a pharmacologically active agent in an infected tissue relative to the concentration of the pharmacologically active agent in the plasma, wherein the method comprises administering (preferably oral administration) the cochleate composition as described herein to a subject having the infected tissue, wherein the concentration of the pharmacologically active agent is at least 25% higher (1.25×), alternatively at least 50% higher (1.5×), alternatively at least 100% higher (2×), alternatively at least 150% higher, alternatively at least 200% higher, alternatively at least 250% higher, alternatively at least 300% higher, alternatively at least 350% higher, alternatively at least 400% higher, alternatively at least 500% higher, alternatively at least 600% higher, alternatively at least 700% higher, alternatively at least 800% higher, or alternatively at least 1000% higher (11×) than the concentration of the pharmacologically active agent in the plasma at 24 hours (alternatively 48 or 72 hours) following administration (preferably oral administration) of the cochleate composition to the subject.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 3 shows various lipid anchored polynucleotides that were made and tested. The polynucleotide depicted in FIG. 3 is a double stranded siRNA specific for the enhanced green fluorescent protein (EGFP). The sense strand of the siRNA has the sequence ACCCUGAAGUUCAUCUGCACC (SEQ ID NO:1), while the antisense strand has the sequence ACUGGGACUUCAAGUAGACGU (SEQ ID NO:2).

DETAILED DESCRIPTION

Figure 1:
FIG. 1 shows a lipid-anchored polynucleotide, having an amphipathic portion and a negatively charged portion. It also shows a phosphatidylserine molecule that can be used to make cochleates. The phosphatidylserine molecule also has an amphipathic portion and a negatively charged portion.
Figure 2:
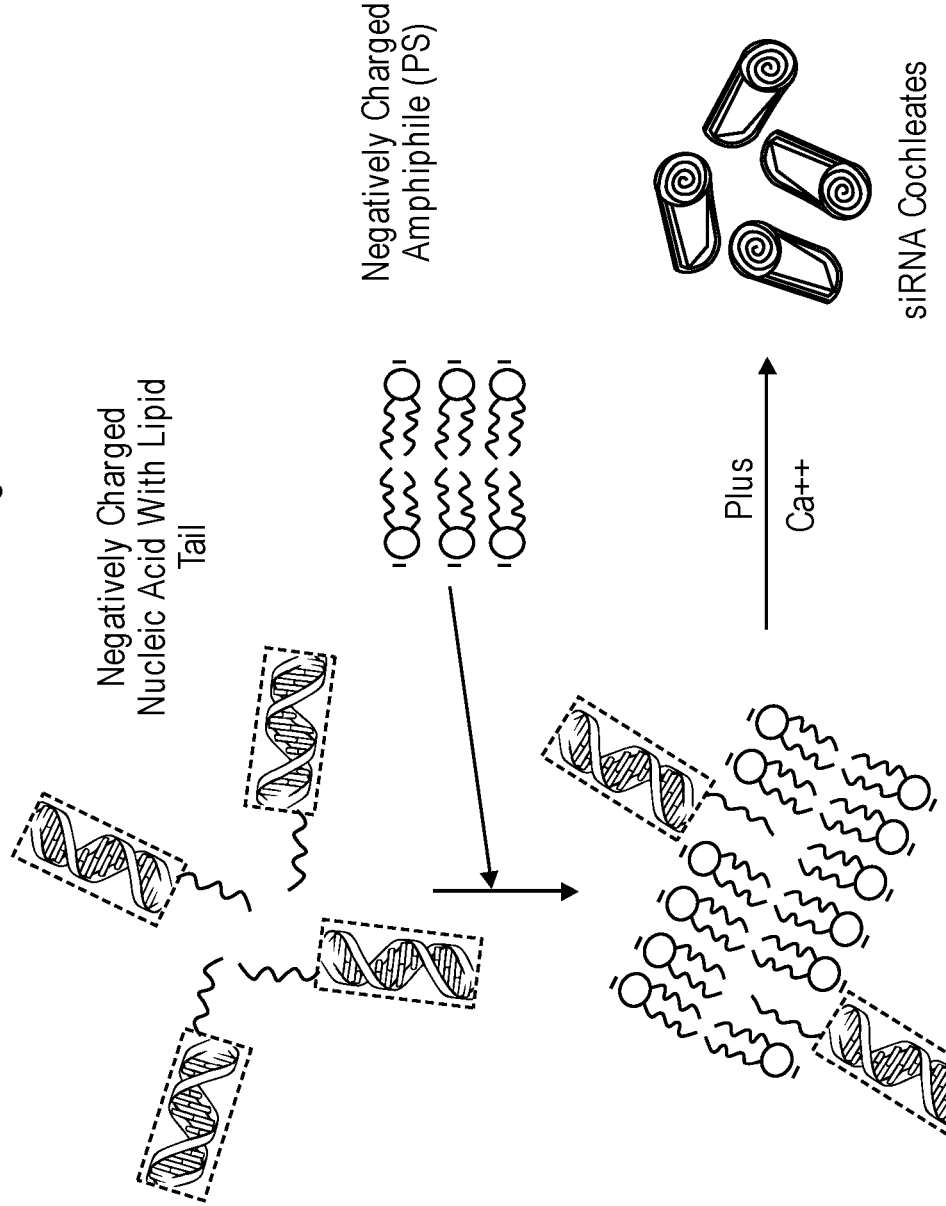
FIG. 2 depicts a schematic representation of how to make cochleates containing a lipid-anchored polynucleotide.

Reference will now be made in detail to various exemplary embodiments, examples of which are illustrated in the accompanying drawings and discussed in the detailed description that follows. It is to be understood that the following detailed description is provided to give the reader a fuller understanding of certain embodiments, features, and details of aspects of the invention, and should not be interpreted as limiting the scope of the invention.

Cochleates form spontaneously through charge-charge interactions (not polymerization) upon the addition of a multivalent cation, such as calcium, to a phospholipid, such as phosphatidylserine. This results in stable, crystalline phospholipid-calcium precipitates, with multilayered structure having a large, continuous, solid, lipid bilayer sheet rolled up in a spiral or as stacked sheets, with no internal aqueous space. This unique structure provides protection from degradation for associated "encochleated" molecules. Since the entire cochleate structure is a series of solid layers, components (e.g., pharmacologically active agents) within the interior of the cochleate structure remain intact, even though the outer layers of the cochleate may be exposed to harsh environmental conditions or enzymes. Divalent calcium concentrations in vivo in serum and mucosal secretions are such that the cochleate structure is maintained. Hence, the majority of cochleate associated molecules are present in the inner layers of a solid, stable, impermeable structure. Following oral administration, cochleates survive extracellular breakdown in the gastrointestinal tract, enter the circulatory system, tissues and activated/infected cells.

Once within the interior of a cell, however, the low intracellular calcium concentration results in the opening of the cochleate and release of the entrapped active pharmacological agent, (The "Trojan-horse effect"). Thus, formulation into cochleates results in intracellular targeting to enhance intracellular drug delivery to infected cells, primarily of monocyte/macrophage lineage and converts injectable drugs into efficacious oral formulations with circulating levels of free drug and therefore low toxicity.

It is possible to control the size of cochleates using size-regulating agents. The absorption rate (absorption efficiency) of the cochleates and their ability to penetrate tissue is mitigated by the size of the crystal or geode cochleate particle. The size of cochleate particles depend on the size of the individual cochleate lipid-crystals, as well as their rate of aggregation and the stability of the aggregates. Unmodified cochleate particles have a relatively hydrophobic surface and in the aqueous cochleate preparation environment the cochleate particles typically stick together and aggregate into particles that are more than several micrometers in diameter, often larger than 10 micrometers and sometimes even larger than 50 micrometers. Larger cochleate particles are not as well absorbed and engulfed by phagocytotic cells than smaller particles.

It was surprisingly found that the size of the individual cochleate crystal as well as their ability to aggregate into larger particles can be regulated by adding one or more size regulating agents, such as a lipid-anchored polynucleotide, a lipid-anchored sugar (glycolipid), or a lipid-anchored polypeptide or a bile salt (such as oxycholate or deoxycholate).

The nano-encapsulation of pharmacologically active agents in lipid-crystal or geode (also known as geodate) cochleate particles, significantly limits the absorption of the pharmacologically active agent (or its first-pass or other metabolites) from the GI tract into the blood stream, and thus reduces or avoids adverse effect resulting from tissue exposure (stomach, intestines, liver, kidney, etc.) or adverse effects from the free pharmacologically active agent and/or its first pass or other metabolites. The lack of blood-stream absorption is demonstrated by relatively low plasma concentrations for the pharmacologically active agent or its metabolites when administered orally as a cochleate formulation as compared to the administration of the same medication in a non-encochleated form.

Cochleate geode or lipid-crystal nano-particles are stable in the GI tract, but poorly absorbed into the blood stream. Without intending to be bound by any theory, it is believed that cochleates are mostly absorbed into the lymphatic system. The lymphatic system absorption is supported by a consistent Tmax for most small molecule medications (or their metabolites) at about 8-12 hours, consistent with the Tmax of fat, such as omega-3 fatty acids.

The absorption of these very small cochleate geodate or lipid-crystal nano-particles into the lymphatic system exposes these particles to macrophages and other phagocytotic cells in the Peyer's patches and other locations in the intestines. Size and surface characteristics of the cochleate particles affect the rate/efficiency at which cochleates are being absorbed in the intestine and lymphatic system, as well as the rate/efficiency at which cochleates are being absorbed by phagocytotic cells.

Because of the circulation within the lymphatic system and chemotaxis, these macrophages and other phagocytotic cells carry the cochleate particles with their medicinal pay-load (pharmacologically active agents) through the lymphatic system to infected or inflamed tissues. Many pathological conditions (such as infection or trauma) are associated with local inflammation in the tissues/organs of concern.

After deposition of the cochleates in the infected or inflamed target tissues, the pharmacological active agent (or its metabolites) leaches into the blood stream. Surprisingly, in contrast to non-encochleated delivery of a pharmacological active agent, it was found that the tissue levels of the pharmacological active agent (or its metabolites) resulting from cochleate delivery increase rapidly following administration as compared to the blood/plasma levels of the pharmacological active agent (or its metabolites).

1. Size-Regulating Agent

A size-regulating agent, as used herein, refers to an agent that reduces the particle size of a cochleate. As used herein, the term "particle size" refers to the particle diameter, or in case the particles are not spherical, to the largest extension in one direction of the particle. The particle size of cochleates can be measured using conventional methods, such as a submicron particle size analyzer.

In certain embodiments, the size regulating agent is a lipid-anchored polynucleotide, a lipid-anchored sugar (glycolipid), or a lipid-anchored polypeptide. In other embodiments the size regulating agent is a bile salt, such as oxycholate or deoxycholate. Bile salts are bile acids compounded with a cation, usually sodium. Bile acids are steroid acids found predominantly in the bile of mammals and are commercially available. In certain embodiments, the lipid-anchored polynucleotide, lipid-anchored sugar, or lipid-anchored polypeptide is also the pharmacologically active agent, including, for example, when the polynucleotide is a double stranded RNA capable of inhibiting the expression of a target gene.

A lipid-anchored polynucleotide is a polynucleotide covalently bound to a fatty acid, a phospholipid, or another compound having a domain that is sufficiently hydrophobic to anchor within the hydrophobic tails of the phospholipid bilayer of the cochleate. A lipid-anchored sugar is a sugar covalently bound to a fatty acid, a phospholipid, or another compound having a domain that is sufficiently hydrophobic to anchor within the hydrophobic tails of the phospholipid bilayer of the cochleate. A lipid-anchored polypeptide is a polypeptide covalently bound to a fatty acid, a phospholipid, or another compound having a domain that is sufficiently hydrophobic to anchor within the hydrophobic tails of the phospholipid bilayer of the cochleate. In certain embodiments, the lipid anchor is selected from the group consisting of a saturated or unsaturated fatty acid having 12-38 carbon atoms, such as palmitate, a sterol, such as cholesterol or lanosterol, and a vitamin, such as vitamin E or vitamin K. In some embodiments, the lipid anchor is directly linked by a covalent bond to the polynucleotide, polypeptide or sugar. In other embodiments, the lipid anchor is indirectly linked to the polynucleotide, polypeptide or sugar by a covalently bound spacer comprising linear molecules including, but not limited to, polycarbon or poly-ethylene glycol chains, such as hexa-ethyleneglycol. The spacer can be linked to the polynucleotide, polypeptide or sugar through ester, amide, ether, or azide bonds.

In some embodiments, the cochleate particle size is optimized by controlling the length of the polynucleotide bound to the anchor-lipid. In certain embodiments the polynucleotide is 15-20 nucleotides, alternatively 15-30 nucleotides, alternatively 20-25 nucleotides, alternatively 30-50 nucleotides in length. In certain embodiments, the polynucleotide has a net negative charge. The oligonucleotide can be RNA or DNA, and the RNA or DNA can be single stranded or double stranded (e.g., a double stranded RNA capable of inhibiting the expression of a target gene).

In other embodiments, the cochleate particle size is optimized by controlling the length or choice of the specific polysaccharide or polypeptide bound to the anchor-lipid. For example, in certain embodiments, the polypeptide is 10-15, alternatively 10-20, alternatively 15-20, alternatively 25-30, alternatively 30-50, or alternatively 20-30 amino acids in length. In certain embodiments, the polypeptide or sugar has a net negative charge. The cochleate particle size can also be optimized by controlling the choice of the specific bile salt, such as oxycholate or deoxycholate.

In one embodiment, at least 50% of cochleates (50% of the total cochleate volume or 50% of pharmacologically active agent-containing cochleate particles) formed with the size-regulating agent have a particle size less than one micron, alternatively less than 2 micron, alternatively less than 5 micron, alternatively less than 10 micron, alternatively less than 20 micron, alternatively less than 25 micron, alternatively less than 50 micron in size. In another embodiment, at least 50% of cochleate particles formed with the size-regulating agent have a particle size between 200-400 nm, 200-600 nm, 200-800 nm, 300-500 nm, 300-700 nm, 300-900 nm, 400-500 nm, 400-600 nm, 400-700 nm, 400-800 nm, 400-900 nm, 500-600 nm, 500-700 nm, 500-800 nm, 500-900 nm, 600-700 nm, 600-800 nm, 600-900 nm, 700-800 nm, or 700-900 nm, and preferably between 400-800 nm.

In another embodiment, at least 75% of cochleates formed with the size-regulating agent have a particle size less than one micron, alternatively less than 2 micron, alternatively less than 5 micron, alternatively less than 10 micron, alternatively less than 20 micron, alternatively less than 25 micron, alternatively less than 50 micron in size. In another embodiment, at least 75% of cochleates formed with the size-regulating agent have a particle size between 200-400 nm, 200-600 nm, 200-800 nm, 300-500 nm, 300-700 nm, 300-900 nm, 400-500 nm, 400-600 nm, 400-700 nm, 400-800 nm, 400-900 nm, 500-600 nm, 500-700 nm, 500-800 nm, 500-900 nm, 600-700 nm, 600-800 nm, 600-900 nm, 700-800 nm, or 700-900 nm, and preferably between 400-800 nm.

In another embodiment, at least 90% of cochleates formed with the size-regulating agent have a particle size less than one micron, alternatively less than 2 micron, alternatively less than 5 micron, alternatively less than 10 micron, alternatively less than 20 micron, alternatively less than 25 micron, alternatively less than 50 micron in size. In another embodiment, at least 90% of cochleates formed with the size-regulating agent have a particle size between 200-400 nm, 200-600 nm, 200-800 nm, 300-500 nm, 300-700 nm, 300-900 nm, 400-500 nm, 400-600 nm, 400-700 nm, 400-800 nm, 400-900 nm, 500-600 nm, 500-700 nm, 500-800 nm, 500-900 nm, 600-700 nm, 600-800 nm, 600-900 nm, 700-800 nm, or 700-900 nm, and preferably between 400-800 nm.

In one embodiments, the median particle size of the cochleate is less than one micron, alternatively less than 2 micron, alternatively less than 5 micron, alternatively less than 10 micron, alternatively less than 20 micron, alternatively less than 25 micron, alternatively less than 50 micron in size. In another embodiment, the median particle size of the cochleate is between 200-400 nm, 200-600 nm, 200-800 nm, 300-500 nm, 300-700 nm, 300-900 nm, 400-500 nm, 400-600 nm, 400-700 nm, 400-800 nm, 400-900 nm, 500-600 nm, 500-700 nm, 500-800 nm, 500-900 nm, 600-700 nm, 600-800 nm, 600-900 nm, 700-800 nm, or 700-900 nm, and preferably between 400-800 nm.

In another embodiment, the mean particle size of the cochleate is less than one micron, alternatively less than 2 micron, alternatively less than 5 micron, alternatively less than 10 micron, alternatively less than 20 micron, alternatively less than 25 micron, alternatively less than 50 micron in size. In another embodiment, the mean particle size of the cochleate is between 200-400 nm, 200-600 nm, 200-800 nm, 300-500 nm, 300-700 nm, 300-900 nm, 400-500 nm, 400-600 nm, 400-700 nm, 400-800 nm, 400-900 nm, 500-600 nm, 500-700 nm, 500-800 nm, 500-900 nm, 600-700 nm, 600-800 nm, 600-900 nm, 700-800 nm, or 700-900 nm, and preferably between 400-800 nm.

In yet another embodiment, the mean particle size of a cochleate with the size reducing agent is 1.5-2 times smaller, alternatively 2-3 times smaller, alternatively 3-5 times smaller, alternatively 2-10 times smaller, alternatively 5-10 times smaller, or alternatively more than 10 times smaller than the mean particle size of the same cochleate without the size reducing agent. In another embodiment, the mean particle size of a cochleate with the size reducing agent is at least 140%, at least 120%, at least 100%, at least 80%, at least 75%, at least 70%, at least 60%, at least 50%, at least 40%, at least 30%, at least 25%, at least 20%, or at least 10% smaller than the mean particle size of the same cochleate without the size reducing agent.

The amount of the size-regulating agent added to the lipid before forming a liposomal suspension or to the liposomal suspension before encochleation can affect the size of the cochleate particles. In certain embodiments, the amount of the size regulating agent is less than 0.1% by weight, alternatively between 0.1% and 0.7%, alternatively between 0.7% and 1.5%, alternatively between 1.5% and 2.5%, alternatively between 2.5% and 5%, alternatively between 5% and 15%, alternatively between 15% and 25%, or alternatively between 25% and 50% by weight of the total cochleate weight. In one embodiment, the amount of the size regulating agent is less than 5% by weight of the total cochleate weight.

2. Methods of Making Cochleates

Cochleates can be made using known methods including, but not limited to, those described in U.S. Pat. Nos. 5,994,318 and 6,153,217, the entire disclosures of which are incorporated herein by reference. In one embodiment, the method generally includes combining a pharmacologically active agent with a lipid (preferably a negatively charged phospholipid, such as phosphatidylserine) in the presence of a solvent, adding an aqueous solution to form liposomes, and precipitating with a multivalent cation to form a cochleate. In another embodiment, the method generally includes combining a pharmacologically active agent with a liposome in the presence of a solvent such that the pharmacologically active agent associates with the liposome, and precipitating with a multivalent cation to form a pharmacologically active agent-containing cochleate.

In a preferred embodiment, the multivalent cation is a divalent metal cation, such as calcium, zinc, magnesium, and barium. In a preferred embodiment, the divalent metal cation is calcium.

The step of introducing a pharmacologically active agent to a liposome in the presence of a solvent can be achieved in a variety of ways. In one embodiment, the pharmacologically active agent is introduced by introducing a solution of the solvent and the pharmacologically active agent to the liposome. Preferably, the liposome is in a liposomal suspension, preferably, an aqueous liposomal suspension. In a preferred embodiment, the solution is introduced to the liposome by dropwise addition of the solution. In other embodiments, the solution can be added by continuous flow or as a bolus. In addition the solution may be introduced to dried lipid, with water added before, after or with the solution.

In another embodiment, the pharmacologically active agent is introduced to the liposome prior to or after the solvent. For example, the pharmacologically active agent may be introduced to a liposomal suspension that includes the solvent. The mixture can then be agitated, mixed, vortexed or the like to facilitate association of the pharmacologically active agent with the liposome. The pharmacologically active agent introduced may be in a powder or a liquid form.

An antioxidant (e.g., Vitamin E) can also be used in making cochleates. The antioxidant can be introduced with the pharmacologically active agent or with the liposome. Preferably, it is incorporated into the liposomal suspension or a solution of the pharmacologically active agent and solvent.

The liposome may be prepared by any known method of preparing liposomes. Thus, the liposomes may be prepared for example by solvent injection, lipid hydration, reverse evaporation, freeze drying by repeated freezing and thawing. The liposomes may be multilamellar (MLV) or unilamellar (ULV), including small unilamellar vesicles (SUV). The concentration of lipid in these liposomal solutions can be from about 0.1 mg/ml to 500 mg/ml. Preferably, the concentration of lipid is from about 0.5 mg/ml to about 50 mg/ml, more preferably from about 1 mg/ml to about 25 mg/ml.

The liposomes may be large unilamellar vesicles (LUV), stable plurilamellar vesicles (SPLV) or oligolamellar vesicles (OLV) prepared, e.g., by detergent removal using dialysis, column chromatography, bio beads SM-2, by reverse phase evaporation (REV), or by formation of intermediate size unilamellar vesicles by high pressure extrusion. Methods in Biochemical Analysis, 33:337 (1988).

Any suitable solvent can be used in these methods. Solvents suitable for a given application can be readily identified by a person of skill in the art. Preferably, the solvent is an FDA acceptable solvent. The solvent can be an organic solvent or an inorganic solvent. In one embodiment, the solvent is a water miscible solvent. In another embodiment, the solvent is water or an aqueous buffer. Other suitable solvents include but are not limited to dimethylsulfoxide (DMSO), a methylpyrrolidone, N-methylpyrrolidone (NMP), acetonitrile, alcohols, e.g., ethanol (EtOH), dimethylformamide (DMF), tetrahydrofuran (THF), and combinations thereof. In general, the pharmacologically active agent concentration within the solvent is between about 0.01 mg/ml and 200 mg/ml. Preferably, the pharmacologically active agent concentration is between about 0.05 mg/ml and about 100 mg/ml, more preferably between about 0.1 mg/ml and 20 mg/ml.

The solvent can optionally be removed, e.g., before the formation of liposomes, at the liposome stage and/or after the cochleates are formed. Any known solvent removal method can be employed. For example, solvent may be removed from the liposomal suspension by tangential flow and/or filtration and/or dialysis, or from the cochleates by washing, filtration, centrifugation, and/or dialysis. The cochleates can be washed, e.g., with buffer or water, optimally with calcium or another cation.

As noted above, a size-regulating agent may be introduced during the method of making the cochleate. In certain embodiments, the size-regulating agent is added to the lipid or liposomes before formation of the precipitated cochleate. For example, in one embodiment, the size-regulating agent is introduced into a liposomal suspension from which cochleates will subsequently be formed (e.g., by addition of cation or dialysis). Alternatively, the size-regulating agent may be introduced to a lipid solution, before of after addition of a pharmacologically active agent.

Any suitable lipid can be used to make the cochleate. In one embodiment, the lipid includes one or more negatively charged lipids. As used herein, the term "negatively charged lipid" includes lipids having a head group bearing a formal negative charge in aqueous solution at an acidic, basic or physiological pH, and also includes lipids having a zwitterionic head group.

The cochleates can also include non-negatively charged lipids (e.g., positive and/or neutral lipids). Preferably, the cochleates include a significant amount of negatively charged lipids. In certain embodiments, a majority of the lipid is negatively charged. In one embodiment, the lipid is a mixture of lipids, comprising at least 50% negatively charged lipid. In another embodiment, the lipid includes at least 75% negatively charged lipid. In other embodiments, the lipid includes at least 85%, 90%, 95% or 98% negatively charged lipid. In yet other embodiments, the lipid includes between 35%-70%, 40%-70%, 45%-65%, 40%-60%, 45%-55%, or 45%-50% negatively charged lipid The negatively charged lipid can include soy-based lipids, other-legume-based lipids, egg-based lipids, bovine-based lipids, or porcine-based lipids. Preferably, the lipid includes phospholipids, such as soy-based phospholipids. The negatively charged lipid can include phosphatidylserine (PS), dioleoylphosphatidylserine (DOPS), phosphatidic acid (PA), phosphatidylinositol (PI), and/or phosphatidyl glycerol (PG) and or a mixture of one or more of these lipids with other lipids. Additionally or alternatively, the lipid can include phosphatidylcholine (PC), phosphatidylethanolamine (PE), diphosphotidylglycerol (DPG), dioleoyl phosphatidic acid (DOPA), distearoyl phosphatidylserine (DSPS), dimyristoyl phosphatidylserine (DMPS), dipalmitoyl phosphatidylglycerol (DPPG) and the like.

3. Pharmacologically Active Agents

Cochleates are preferably associated with or loaded with a pharmacologically active agent. For example, the pharmacologically active agent may be selected from one of the following classes: an anti-fungal, an anti-bacterial, including but not limited to a beta-lactamase inhibitor, an anti-viral, an anti-parasitic, anti-protozoal or antihelminthic, a vaccine, an anti-inflammatory agent, a polynucleotide, including, but not limited to a siRNA, iRNA, anti-sense therapy (RNA or DNA, single stranded or double stranded), or gene-therapy polynucleotide (integrating DNA or DNA plasmids), an immunotherapy, an anti-cancer agent (including anti-neoplastic agents), an anti-dyslipidemia agent, an anti-dementia agent, a nutritional supplement, an herbal product, or a vitamin.

In certain embodiments, the lipid-anchored polynucleotide, lipid-anchored sugar, or lipid-anchored polypeptide is the pharmacologically active agent, including, for example, when the polynucleotide is a double stranded RNA capable of inhibiting the expression of a target gene.

By way of example, the anti-fungal agent can include, but is not limited to, one or more of the following: a polyene anti-fungal (such as nystatin, natamycin, SPA-S-843, SPA-S-752, SPA-S-753, or partricin A or partricin B), an echinocandin (such as anidulafungin, caspofungin, micafungin, or biafungin), an azole antifungal (such as fluconazole, ketoconazole, voriconazole, posaconazole, isavuconazole, bifonazole, butoconazole, clotrimazole, econazole, fenticonazole, isoconazole, luliconazole, miconazole, omoconazole, oxiconazole, sertaconazole, sulconazole, tioconazole, albaconazole, efinaconazole, epoxiconazole, itraconazole, propiconazole, ravuconazole, terconazole, or abafungin), a naphthoquinone (such as atovaquone), a 1,3 D glucan synthesis inhibitor (such as enfumafungin or its derivatives (MK-3118 or SCY-078), a 14α-demethylase inhibitor, or an ergosterol production inhibitor (such as an azole antifungal, or metalloenzyme fungal CYP51 inhibitors like VT-1161, VT-1129, VT-1598).

By way of example, the anti-bacterial agent can include, but is not limited to, one or more of the following: a protein synthesis inhibitors; a 30S initiation inhibitor, such as aminoglycoside antibiotics (including streptomycin, dihydrostreptomycin, neomycin, framycetin, paromomycin, ribostamycin, kanamycin, amikacin, arbekacin, bekanamycin, dibekacin, tobramycin, spectinomycin, hygromycin B, paromomycin, gentamicin, netilmicin, sisomicin, isepamicin, verdamicin, and astromicin); a 30S tRNA binding antibiotic, such as tetracyclines, glycylcyclines, or fluorocyclines (including doxycycline, chlortetracycline, clomocycline, demeclocycline, lymecycline, meclocycline, metacycline, minocycline, oxytetracycline, penimepicycline, rolitetracycline, tetracycline, tigecycline, or eravacycline); a 50S initiation inhibitor, such as oxazolidinone antibiotics (including eperezolid, linezolid, posizolid, radezolid, ranbezolid, sutezolid, and tedizolid); a peptidyl transferase, such as amphenicols or pleuromutilins (including chloramphenicol, azidamfenicol, thiamphenicol, florfenicol, retapamulin, tiamulin, and valnemulin); a transpeptidation/translocation antibiotic, such as macrolides, ketolides, fluoroketolides, lincosamides or streptogramins (including azithromycin, clarithromycin, dirithromycin, erythromycin, flurithromycin, josamycin, midecamycin, miocamycin, oleandomycin, okitamycin, roxithromycin, spiramycin, troleandomycin, tylosin, telithromycin, cethromycin, solithromycin, fidaxomicin, carbomycin A, kitasamycin, clindamycin, lincomycin, pirlimycin, pristinamycin, quinupristin, dalfopristin, and virginiamycin); an elongation factor inhibitor, such as steroid antibacterials (including fusidic acid); a peptidoglycan synthesis/transpeptidases inhibitor, such as a penicillin (including natural penicillins penicillin G and penicillin V; β-lactamase-resistant penicillins methicillin, nafcillin, oxacillin, cloxacillin and dicloxacillin; aminopenicillins ampicillin, amoxicillin, pivampicillin, hetacillin, bacampicillin, metampicillin, talampicillin and epicillin; carboxypenicillins carbenicillin, and ticarcillin; ureidopenicillins mezlocillin and piperacillin) or a cehphalosporin (including cephacetrile, cefadroxyl, cephalexin, cephaloglycin, cephalonium, cephaloradine, cephalothin, cephapirin, Cefatrizine, Cefazaflur, Cefazedone, cephazolin, cephradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin); a penems or carbapenem (including faropenem, ertapenem, doripenem, imipenem, meropenem, biapenem, and panipenem); a monobactam (including aztreonam, tigemonam, carumonam, nocardicin A); a glycopeptide antibiotic (including vancomycin, oritavancin, telavancin, teicoplanin, dalbavancin, and ramoplanin); a beta-lactamase inhibitor (including clavulanate, sulbactam, tazobactam, and avibactam), an other antibiotic (including: fosfomycin, cycloserine, bacitracin, colistin, polymyxin B, daptomycin, lysozyme, gramicidin, isoniazid, or teixobactin).

By way of example, the anti-viral agent can include, but is not limited to, one or more of the following: a DNA polymerase inhibitor (such as acyclovir, famciclovir, H2G, valciclovir, ganciclovir, cidofovir, or brincidofovir); an uncoating inhibitor (such as amantadine and rimantadine), a viral entry inhibitor (such as enfuvirtide), an immune response modifier (such as imiquimod, resiquimod, or rardiquimod) a nucleoside reverse transcriptase inhibitor (such as zidovudine or lamivudine), or one of the following; sofosbuvir, ledipasvir, simeprevir, ombitasvir, paritaprevir, ritonavir, abacavir, dolutegravir, tenofovir, emtricitabine, elvitegravir, maraviroc, efavirenz, rilpivirine, cobicistat, fosampremavir, nelfinavir, delavirdine, indinavir, raltegravir, interferon gamma, ribavirin, boceprevir, efavirenz, entecavir, daclatasvir, atazanavir. The antiviral agent can also be any HIV antiviral agent.

By way of example, the anti-parasitic, anti-protozoal or anti-helminthic agent can include, but is not limited to, one or more of the following: a benzimidazole derivative (such as albendazole, mebendazole, thiabendazole, fenbendazole, triclabendazole, or flubendazole), an avermectin analog or derivative (such as avermectin, abamectin, or ivermectin), diethylcarbamazine, suramin, pyrantel pamoate, proguanil, levamisole, a salicylanilide (such as niclosamide, or oxyclozanide), praziquantel, an octadepsipeptide (such as emodepside), a naphthoquinone (such as atovaquone), an aminoacetonitrile derivative (such as monepantel), a spiroindole (such as derquantel), or pelletierine sulphate.

By way of example, in one embodiment, the anti-inflammatory agent can include, but is not limited to, one or more of the following: an NSAID, including an NSAID which belongs to is one or more of the following classes: a Salicylate (such as aspirin [acetylsalicylic acid], diflunisal, salsalate or salicylic acid and other salicylates), a propionic acid derivative (such as ibuprofen, dexibuprofen, naproxen, fenoprofen, ketoprofen, dexketoprofen, flurbiprofen, oxaprozin, or loxoprofen), an acetic acid derivative (such as indomethacin, tolmetin, sulindac, etodolac, ketorolac, diclofenac, aceclofenac, or nabumetone), an enolic acid (-oxicam) derivative (such as piroxicam, meloxicam, tenoxicam, droxicam, lornoxicam, isoxicam, or phenylbutazone), an anthranilic acid derivative (e.g., a fenamate, such as mefenamic acid, meclofenamic acid, flufenamic acid, or tolfenamic acid), a selective COX-2 inhibitor (such as celecoxib, rofecoxib, valdecoxib, parecoxib, lumiracoxib, etoricoxib, or firocoxib), a sulfonanilide (such as nimesulide) or others (such as clonixin, licofelone or H-harpagide).

By way of example, in another embodiment, the anti-inflammatory agent can include, but is not limited to, one or more of the following: a corticosteroid (such as hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, prednicarbate, flunisolide, fluticasone furoate, fluticasone propionate, triamcinolone acetonide, beclomethasone dipropionate, and budesonide), a DMARD (such as methotrexate, azathioprine, ciclosporin, penicillamine, auranofin, aurothiomalate salts, minocycline, hydroxychloroquine, chloroquine, sulfasalazine, leflunomide, teriflunomide, mesalamine, or cyclophosphamide), acetaminophen, an anti-TNF agent (such as adalimumab, infliximab, etanercept, certolizumab pegol), a macrolide calcineruin inhibitor (such as sirolimus or tacrolimus), a JAK-inhibitor (such as tofacitinib, Ruxolitinib, Baricitinib (LY3009104, INCB28050), CYT387, Filgotinib (GLPG0634), GSK2586184, Lestaurtinib, Pacritinib (SB1518), TG101348, JSI-124, or CHZ868), an IL-6 antagoinst (such as tocilizumab or atlizumab), an anti-CD20 agent (such as rituximab, obinutuzumab, Ibritumomab tiuxetan, tositumomab, ofatumumab, ocrelizumab, TRU-015, or IMMU-106 [veltuzumab]), a CD52-antagonist (such as alemtuzumab), an alpha-4 integrin antagonist (such as natalizumab), a type II topoisomerase inhibitor (such as mitoxantrone), a sphingosine-1-phosphate receptor modulator (such as fingolimod, laquinimod, ozanimod, or ponesimod), a beta-interferon, or one of the following agents or their functional similars: glatiramer acetate or dimethyl fumarate.

4. Pharmaceutical Compositions

The cochleates described herein can be prepared as a pharmaceutical composition. Suitable preparation forms for the pharmaceutical compositions disclosed herein include, for example, tablets, capsules, soft capsules, granules, powders, suspensions, emulsions, microemulsions, nanoemulsions, unit dosage forms, rings, films, suppositories, solutions, creams, syrups, transdermal patches, ointments and gels.

The pharmaceutical compositions can include other pharmaceutically acceptable excipients, such as, a buffer (e.g., Tris-HCl, acetate, phosphate) of various pH and ionic strength; an additive such as albumin or gelatin to prevent absorption to surfaces; a protease inhibitor; a permeation enhancer; a solubilizing agent (e.g., glycerol, polyethylene glycerol); an anti-oxidant (e.g., ascorbic acid, sodium metabisulfite, butylated hydroxyanisole); a stabilizer (e.g., hydroxypropyl cellulose, hydroxypropylmethyl cellulose); a viscosity increasing agent (e.g., carbomer, colloidal silicon dioxide, ethyl cellulose, guar gum); a sweetener (e.g. aspartame, citric acid); a preservative (e.g., Thimerosal, benzyl alcohol, parabens); a flow-aid (e.g., colloidal silicon dioxide), a plasticizer (e.g., diethyl phthalate, triethyl citrate); an emulsifier (e.g., carbomer, hydroxypropyl cellulose, sodium lauryl sulfate); a polymer coating (e.g., poloxamers or poloxamines, hypromellose acetate succinate); a coating and film forming agent (e.g., ethyl cellulose, acrylates, polymethacrylates, hypromellose acetate succinate); an adjuvant; a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters such as ethyl oleate) solution, suspension, emulsion or oil; and a parenteral vehicle (for subcutaneous, intravenous, intraarterial, or intramuscular injection), including but not limited to, sodium chloride solution, Ringer's dextrose, dextrose and sodium chloride, lactated Ringer's and fixed oils.

These excipients are provided by way of example and it will be known to those of skill in the art that there will be other or different excipients that can provide the same chemical features as those listed herein.

5. Dosage and Administration

A pharmaceutical composition comprising a cochleate, as disclosed herein, is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intraperitoneal, intraventricular, intraepidural, or others as well as oral, nasal, ophthalmic, rectal, or topical.

In one embodiment, the cochleate is administered orally, for example, by administering a suspension, a tablet, a capsule, a softgel or other oral dosage form. In other embodiments, the encochleated medication is administered parenterally, by infusion or injection into the bloodstream, the eye, the peritoneal cavity, into the muscle or subcutaneously. In yet other embodiments, the encochleated medication is administered topically, such as dripped onto the eye, into the ear, or applied to the skin, toe/finger-nails or genital areas in a variety of forms such as a patch (layer or reservoir), cream, ointment, or suspension, or as per anal suppository.

With the significantly enhanced tissue penetration provided by the cochleates as described herein, it will now be possible to provide a lower daily dosage of the pharmacologically active agent and still achieve pharmaceutically effective levels of the pharmacologically active agent.

The targeted delivery of encochleated medications significantly limits absorption into the blood stream and results in a surprisingly rapid penetration of the administered encochleated medication into targeted tissues (typically inflamed, infected, traumatized or rapidly growing/cancerous tissues), as compared to oral administration of the non-encochleated form of the same medication or even injectable forms of such medication.

In some embodiments, the tissue level of a pharmacologically active agent (or its metabolites) delivered by a cochleate is higher than the blood/plasma/serum level of the pharmacologically active agent (or its metabolites) as determined within the same subject or group of subjects. In embodiments, the tissue level of the pharmacologically active agent following oral administration of the cochleate composition is at least 50%, alternatively at least 60%, alternatively at least 70%, alternatively at least 75%, alternatively at least 80%, alternatively at least 90%, alternatively at least 100%, alternatively at least 110%, alternatively at least 120%, alternatively at least 125%, alternatively at least 130%, alternatively at least 140%, alternatively at least 150%, alternatively at least 200%, alternatively at least 500%, alternatively at least 600%, alternatively at least 750%, or alternatively at least 1000% of the plasma levels. In one embodiment, the tissue level of the pharmacologically active agent following oral administration of the cochleate composition is 2 times higher than the plasma level of the pharmacologically active agent. In another embodiment, the pharmacologically active agent specifically excludes amphotericin B.

In some embodiments, the tissue level of a pharmacologically active agent (or its metabolites) delivered by a cochleate is higher than the tissue level resulting from non-encochleated delivery of the same pharmacologically active agent (or its metabolites). Thus, in some embodiments, encochleated medications resolve medical conditions earlier than a non-encochleated version of the same medication.

Whereas the dissemination of non-encochleated medications is often mostly the result of absorption, dissipation, migration, metabolization and excretion processes that are generally similar in healthy versus sick subjects, the same is generally not true for encochleated medications. As a result, tissue levels and clearance processes develop differently in healthy compared to sick subjects (subjects with a medical condition) when treated with encochleated medications.

In some embodiments, the tissue level of a pharmacologically active agent (or its metabolites) delivered by a cochleate to a subject with a medical condition is higher than the level of the pharmacologically active agent (or its metabolites) in the comparative tissues of a healthy subject upon administration of the same encochleated medication. In certain embodiments, the tissue level of a pharmacologically active agent (or its metabolites) at 24 hours following administration via cochleates to a subject with a medical condition is at least 25% higher, alternatively at least 50% higher, alternatively at least 100% higher, alternatively at least 150% higher, alternatively at least 200% higher, alternatively at least 250% higher, alternatively at least 300% higher, alternatively at least 350% higher, alternatively at least 400% higher, alternatively at least 500% higher, alternatively at least 600% higher, alternatively at least 700% higher, alternatively at least 800% higher, alternatively at least 1000% higher, as compared to the tissue level of the pharmacologically active agent (or its metabolites) at 24 hours (alternatively at 48 or 72 hours) following administration by cochleates to a healthy subject. In one embodiment, the pharmacologically active agent specifically excludes amphotericin B.

In other embodiments, when treated with the same encochleated medication, blood/plasma/serum levels of this medication in the subject or subjects with a medical condition are lower than in healthy subjects. In yet other embodiments, when treated with the same encochleated medication, urine levels of this medication in the subject or subjects with a medical condition are lower than in healthy subjects.

Thus, the levels of encochleated medications in targeted tissues (e.g, an infected or inflamed tissue) are differentially higher as compared to the levels of encochleated medication in plasma or encochleated medication in tissue from a healthy subject or the tissue levels of non-encochleated medications.

Tissue levels of the pharmacologically active agent may be determined in a range of tissues, organs, and bodily fluids, including but not limited to: kidney, lung, sputum, liver, brain, spine, spinal fluid, nerve, spleen, heart, thymus, lymph node, arterial wall, pancreas, gall bladder, prostate, ovary, uterus, female breast, testicle, thyroid, adrenal gland, hypothalamus, pituitary gland, eye, ear, intestine, bladder, urine, muscle, skin, white blood cells, bone, cartilage, joint tissue, synovial fluid, adipose tissue or tumors and cancerous/neoplastic tissues in various forms.

In certain embodiments, tissue penetration and tissue levels of the pharmacologically active agent (or its metabolites) are determined based on tissue concentration at certain time points, maximum tissue concentration (Cmax), and/or cumulative tissue concentration over a specified time (AUC). In certain embodiments, the differentially higher tissue levels are observed during the first day after administration, demonstrating rapid penetration of the administered encochleated medication into targeted tissues. In other embodiments these higher tissue levels are observed within the first 2 days, alternatively within the first 3 days after administration, alternatively within the first 5 days after administration, alternatively within the first 7 days after administration, alternatively within the first 10 days after administration, alternatively within the first 15 days after administration, or alternatively within the first 30 days after administration. In yet other embodiments the higher tissue levels are observed on day 1, alternatively, on day 2, 3, 4, 5, 6, 7, 8, 9, 10, 11, 12, 14, 15, 20, 25, or on day 30. In one embodiment, the pharmacologically active agent specifically excludes amphotericin B.

While encochleated medications penetrate target tissues more rapidly early on in the treatment cycle and result in higher tissue levels during the early stage of pharmacological intervention, with the consequential earlier resolution of the treated medical condition, the tissue levels will decline earlier than with comparative treatment with non-encochleated medications. In some embodiments, the more modest tissue levels during later stages of treatment with encochleated medication results in lower toxicity and better functionality of sensitive organs and tissues, thus improving the survival prospect and health of the treated subject.

In some embodiments, such lower levels associated with the beginning of resolution of the medical condition become apparent within 3 days after initiation of treatment with an encochleated medication as compared to treatment with a non-encochleated version of this medication. Alternatively, in other embodiments such lower tissue levels associated with the beginning of resolution of the medical condition become apparent within 5 days after initiation of treatment with an encochleated medication, alternatively within 7 days, alternatively within 10 days, alternatively within 15 days, alternatively within 20 days, alternatively within 30 days, alternatively within 50 days as compared to treatment with a non-encochleated version of this medication. In one embodiment, the pharmacologically active agent specifically excludes amphotericin B.

6. Method of Treatment

The cochleates as described herein can be used in a method of treating a subject at risk of (or susceptible to) a disorder or having a disorder which can be treated with a pharmacologically active agent. Any therapeutic indication that would benefit from a pharmaceutically active agent can be treated using the cochleates descried herein. Therapeutic indications include, but are not limited to, bacterial, fungal, viral, or parasitic infections, inflammation associated with auto-immune or other conditions, resolution of trauma, or remission of cancers and neoplastic conditions.

In certain embodiments, the method comprises administering a cochleate comprising a pharmacologically active agent and a size reducing agent to a subject. The cochleates and cochleate compositions of the present invention may be administered orally, nasally, topically, intravenously, transdermally, buccally, sublingually, rectally, vaginally or parenterally. In a preferred embodiment, the cochleate is administered orally. The subject is a human or non-human animal, such as dogs, cats, and farm animals. In a preferred embodiment, the subject is a human.

EXAMPLES

The examples provided above are simply for illustrative purposes. Those of skill in the art will be able to readily determine appropriate methods and equipment in order to produce suitable solid dispersion forms as described herein.

Example 1

Regulation of Particle Size of Cochleates with Lipid-Anchored Polynucleotides siRNA was covalently coupled to a lipid anchor. The siRNA was a double-stranded RNA molecule having 21 nucleotides with 2 nucleotide overhangs at each 3' end. The siRNA is specific for the enhanced green fluorescent protein (EGFP). The sense strand has the sequence ACC-CUGAAGUUCAUCUGCACC (SEQ ID NO:1), while the antisense strand has the sequence ACUGGGACUUCA-AGUAGACGU (SEQ ID NO:2). The siRNA was covalently bound to various lipid anchors, including palmitate with or without S18, cholesterol with or without S18, vitamin E (racemic) with or without S18, or vitamin EL (L-isomer of vitamin E) with or without S18. S18 is an 18 atom hexaethyleneglycol spacer having the following formula:

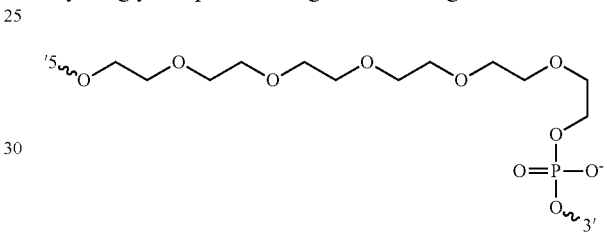

The lipid-anchored siRNA also included a fluorescent Cy3 dye. The lipid-anchored siRNA in aqueous solution was added to a suspension of liposomes, followed by the addition of calcium to the siRNA-liposome complexes to form cochleates. The liposomes were composed of DOPS (dioleoylphosphatidylserine, 99.9% pure) or DOPS plus 10% (wt:wt) cholesterol. Phase contrast and fluorescence microscopy were used to evaluate themorphology of the siRNA-cochleate formulations at the liposome, cochleate, and "opened cochleate" (after EDTA addition) stages.

Particle size of the cochleates was measured using a Photon Correlation Spectroscopy submicron particle size analyzer. Samples were run through the analyzer at a 90° angle, at 22° C., with a run time of 200 seconds. The diluent was an aqueous solution containing 4 mM calcium.

Plain cochleates, because of their hydrophobic surfaces, aggregate in aqueous solution. Thus, control cochleates containing no siRNA formed large, cochleate aggregates following the addition of calcium (data not shown). The average particle size of control cochleates containing no lipid-anchored polynucleotide was about 85-115 μm. The mean particle size of cochleates formed with different lipid-anchored polynucleotides was on the order of 100-200 fold smaller than the control cochleates, as set forth in the table below.

| Lipid-Anchored Polynucleotide | Mean Size (nm) | Mean SD (nm) |
|---|---|---|
| EGFP-VEL | 714.8 | 465.6 |
| EGFP-VEL + CH | 759.8 | 331.3 |
| EGFP-VEL + S18 | 449.7 | 327.6 |
| EGFP-VEL + S18 + CH | 443.9 | 336.0 |
| EGFP-VE | 496.0 | 335.9 |
| EGFP-VE + CH | 667.7 | 389.2 |
| EGFP-VE + S18 | 399.9 | 284.7 |

-continued

| Lipid-Anchored Polynucleotide | Mean Size (nm) | Mean SD (nm) |
|---|---|---|
| EGFP-VE + S18 + CH | 1453.1 | 1077.1 |
| PMA1-1I + CH | 3000.0 | 173.0 |
| EGFP-1Pal + CH | 758.3 | 216.6 |

CH denotes that cochleates were made with cholesterol in the lipid bilayer.

Example 2

Reducing Particle Size of Amphotericin B Cochleates Made with Deoxycholate

Cochleates containing amphotericin B (CAmB) and different amounts of deoxycholate were prepared. To prepare CAmB containing 0.45 mg/ml deoxycholate in the final product, 20 mg of Amphotericin B in 0.5 ml 50 mM NaOH solution was combined with 100 mg of 50% soy phosphatidylserine liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. In order to make particle size of the amphotericin B cochleate crystals smaller, 5.0 mg deoxycholate in 83 µl sterile water was then added to the mixture of the amphotericin B liposome. To the resultant mixture, 0.378 ml of 1M calcium chloride solution was then added with vigorous mixing to form amphotericin B cochleates. The ratio of lipids to amphotericin B in the cochleates was 5:1, and they contained 0.45 mg/ml deoxycholate in the final product.

To prepare CAmB containing 0.9 mg/ml deoxycholate in the final product, 20 mg of Amphotericin B in 0.5 ml 50 mM NaOH solution was combined with 100 mg of 50% soy PS liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. In order to make particle size of the amphotericin B cochleate crystals smaller, 10 mg deoxycholate in 167 µl sterile water was then added to the mixture of the amphotericin B liposome. To the resultant mixture, 0.378 ml of 1M calcium chloride solution was then added with vigorous mixing to form amphotericin B cochleates. The ratio of lipids to amphotericin B in the cochleates was 5:1, and they contained 0.9 mg/ml deoxycholate in the final product.

To prepare CAmB containing 1.79 mg/ml deoxycholate in the final product, 20 mg of Amphotericin B in 0.5 ml 50 mM NaOH solution was combined with 100 mg of 50% soy PS liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. In order to make particle size of the amphotericin B cochleate crystals smaller, 20 mg deoxycholate in 0.33 ml sterile water was then added to the mixture of the amphotericin B liposome. To the resultant mixture, 0.378 ml of 1M calcium chloride solution was then added with vigorous mixing to form amphotericin B cochleates. The ratio of lipids to amphotericin B in the cochleates was 5:1, and they contained 1.79 mg/ml deoxycholate in the final product.

To prepare CAmB containing 2.5 mg/ml deoxycholate in the final product, 20 mg of Amphotericin B in 0.5 ml 50 mM NaOH solution was combined with 100 mg of 50% soy PS liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. In order to make particle size of the amphotericin B cochleate crystals smaller, 30 mg deoxycholate in 0.5 ml sterile water was then added to the mixture of the amphotericin B liposome. To the resultant mixture, 0.378 ml of 1M calcium chloride solution was then added with vigorous mixing to form amphotericin B cochleates. The ratio of lipids to amphotericin B in the cochleates was 5:1, they and contained 2.5 mg/ml deoxycholate in the final product.

To prepare CAmB containing 3.4 mg/ml deoxycholate in the final product, 20 mg of Amphotericin B in 0.5 ml 50 mM NaOH solution was combined with 100 mg of 50% soy PS liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. In order to make particle size of the amphotericin B cochleate crystals smaller, 40 mg deoxycholate in 0.67 ml sterile water was then added to the mixture of the amphotericin B liposome. To the resultant mixture, 0.378 ml of 1M calcium chloride solution was then added with vigorous mixing to form amphotericin B cochleates. The ratio of lipids to amphotericin B in the cochleates was 5:1, and they contained 3.4 mg/ml deoxycholate in the final product.

To prepare CAmB containing 4.3 mg/ml deoxycholate in the final product, 20 mg of Amphotericin B in 0.5 ml 50 mM NaOH solution was combined with 100 mg of 50% soy PS liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. In order to make particle size of the amphotericin B cochleate crystals smaller, 50 mg deoxycholate in 0.83 ml sterile water was then added to the mixture of the amphotericin B liposome. To the resultant mixture, 0.378 ml of 1M calcium chloride solution was then added with vigorous mixing to form amphotericin B cochleates. The ratio of lipids to amphotericin B in the cochleates was 5:1, and they contained 4.3 mg/ml deoxycholate in the final product.

To prepare CAmB containing 5 mg/ml deoxycholate in the final product, 20 mg of Amphotericin B in 0.5 ml 50 mM NaOH solution was combined with 100 mg of 50% soy PS liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. In order to make particle size of the amphotericin B cochleate crystals smaller, 60 mg deoxycholate in 1.0 ml sterile water was then added to the mixture of the amphotericin B liposome. To the resultant mixture, 0.378 ml of 1M calcium chloride solution was then added with vigorous mixing to form amphotericin B cochleates. The ratio of lipids to amphotericin B in the cochleates was 5:1, and they contained 5 mg/ml deoxycholate in the final product.

To prepare CAmB containing no deoxycholate in the final product, 20 mg of Amphotericin B in 0.5 ml 50 mM NaOH solution was combined with 100 mg of 50% soy PS liposome in 10 ml 50 mM phosphate buffer (the soy PS liposome was filtered through 5, 0.8 and 0.45 µm filters) to form liposomes containing the Amphotericin B. 120 µg vitamin E in 1.2 µl alcohol was added into the AmB liposome. To the resultant mixture, 0.378 ml of 1M calcium chloride solution was then added with vigorous mixing to form amphotericin B cochleates. The ratio of lipids to amphotericin B in the cochleates was 5:1.

Particle size of the cochleates was measured using a submicron particle size analyzer. Surprisingly, when deoxycholate was used to make the cochleates with amphotericin B, it was possible to reduce the particle size to 8.7 µm (mean) or 7.8 µm (median), about 2-3 times smaller than amphotericin B cochleates made without deoxycholate. This is also over 10 times smaller than the particle size of amikacin cochleates made with deoxycholate (see Example 3).

| Cochleate Formulation | Size <10% | 25% | 50% | 75% | 90% | Mean | Median |
|---|---|---|---|---|---|---|---|
| CamB w/o Deoxycholate | 7.5 μm | 12.5 μm | 19.2 μm | 26.3 μm | 32.7 μm | 19.2 μm | 19.7 μm |
| CamB with 0.45 mg/ml Deoxycholate | 4.9 μm | 7.2 μm | 10.9 μm | 15.7 μm | 22 μm | 13 μm | 10.9 μm |
| CamB with 0.9 mg/ml Deoxycholate | 4.3 μm | 6.4 μm | 9.8 μm | 15 μm | 27.8 μm | 12.8 μm | 9.8 μm |
| CamB with 1.8 mg/ml Deoxycholate | 2.7 μm | 4.8 μm | 7.8 μm | 11.7 μm | 15.9 μm | 8.8 μm | 7.8 μm |
| CamB with 2.5 mg/ml Deoxycholate | 2.5 μm | 4.8 μm | 8.1 μm | 12.2 μm | 15.8 μm | 8.7 μm | 8.1 μm |
| CamB with 3.4 mg/ml Deoxycholate | 2.7 μm | 5.3 μm | 8.8 μm | 13.2 μm | 18 μm | 9.8 μm | 8.8 μm |
| CamB with 4.5 mg/ml Deoxycholate | 3.3 μm | 5.4 μm | 8.4 μm | 11.9 μm | 15.2 μm | 8.8 μm | 8.4 μm |
| CAmB with 5 mg/ml Deoxycholate | 4.4 μm | 7.2 μm | 10.2 μm | 13.3 μm | 16.3 μm | 10.3 μm | 10.2 μm |

Example 3

Particle Size Analysis for Amikacin Cochleates Made with Deoxycholate

To prepare amikacin cochleates, 2 mg of amikacin 0.2 ml sterile water was filtered through a 0.22 μm filter and combined with 20 mg of 50% soy PS liposomes in 2.0 ml sterile water (the soy PS liposome suspension was first filtered through 5, 0.8 and 0.45 μm filters) to form liposomes containing amikacin. Deoxycholate was added at different times during the process of making the cochleates: before adding the amikacin, before adding calcium, after adding calcium, or at each step, as shown in the table below. To the resultant mixture. 0.159 ml of 0.11 calcium chloride was then added with vigorous mixing to form amikacin cochleates. A control cochleate (placebo) containing no amikacin was also prepared and deoxycholate was added before the calcium. Other control cochleates were prepared having amikacin and no deoxycholate or no amikacin and no deoxycholate. Particle size of the cochleates was measured using a submicron particle size analyzer.

Amikacin cochleates form large aggregates and average about 50-80 μm in size without the addition of deoxycholate, depending on the ratio of lipid to amikacin and the final pH. Surprisingly, adding deoxycholate to the large amikacin cochleates did not reduce their size but actually increased their size to an average of about 85-117 μm depending on when the deoxycholate was added. As noted above, the particle size of amphotericin B cochleates made with deoxycholate was about at least 10 times smaller than the particle size of amikacin cochleates made with deoxycholate.

Example 4

Pharmacokinetic (PK) and Biodistribution (BD) Following Oral Dosing of Encochleated Amphotericin B (CAmB) in Mice with Systemic Candidiasis Amphotericin B deoxycholate (DAmB) has been considered the "gold standard" in antifungal treatments due to its broad spectrum of activity and limited resistance. However, the use of DAmb and its derivatives is limited by significant

| Sample Info | Size <10% | 25% | 50% | 75% | 90% | Mean | Median |
|---|---|---|---|---|---|---|---|
| CAmK - add Deoxycholate before Amk | 43.8 μm | 64 μm | 85.6 μm | 110 μm | 134.8 μm | 87 μm | 85.6 μm |
| CAmK - add Deoxycholate before Ca++ | 45.2 μm | 90.1 μm | 121.7 μm | 152 μm | 178.3 μm | 117.7 μm | 121.7 μm |
| CAmK - add Deoxycholate After Ca++ | 43.2 μm | 65 μm | 85.8 μm | 107.4 μm | 127.5 μm | 84.9 μm | 85.8 μm |
| CAmK - add Deoxycholate in each step | 46.5 μm | 70 μm | 91.1 μm | 113.8 μm | 135.6 μm | 90.5 μm | 91.1 μm |
| Placebo - add Deoxycholate before Ca++ | 16.2 μm | 69.6 μm | 110.9 μm | 156.9 μm | 198.2 μm | 110.6 μm | 110.9 μm |
| 4:1 CAmK - 10 mgPS/ml final pH 5.0 (no deoxycholate) | 27 μm | 53.2 μm | 75.7 μm | 98.9 μm | 121.3 μm | 75.5 μm | 75.7 μm |
| 4:1 CAmK - 10 mgPS/ml final pH 7.0 (no deoxycholate) | 17.5 μm | 35.2 μm | 51.3 μm | 71.3 μm | 95.1 μm | 54.7 μm | 51.3 μm |
| 4:1 CAmK - 20 mgPS/ml final pH 5.0 (no deoxycholate) | 24.1 μm | 49 μm | 77.2 μm | 111.8 μm | 145.9 μm | 82 μm | 77.2 μm |
| 4:1 CAmK - 20 mgPS/ml final pH 7.0 (no deoxycholate) | 33.1 μm | 52.1 μm | 72.2 μm | 95.5 μm | 118.9 μm | 73.8 μm | 72.2 μm |
| 10:1 CAmK - 10 mgPS/ml final pH 5.0 (no deoxycholate) | 16.7 μm | 40.1 μm | 61.8 μm | 84.5 μm | 106.5 μm | 62.7 μm | 61.8 μm |
| 10:1 CAmK - 10 mgPS/ml final pH 7.0 (no deoxycholate) | 13.6 μm | 37.1 μm | 64.6 μm | 90.6 μm | 115.1 μm | 65.2 μm | 64.6 μm |
| Placebo - 10 mgPS/ml final pH 5.0 (no deoxycholate) | 13.4 μm | 30.5 μm | 94.4 μm | 197.4 μm | 278.3 μm | 122.9 μm | 94.4 μm |
| Placebo - 20 mgPS/ml final pH 5.0 (no deoxycholate) | 15.3 μm | 57.2 μm | 119.6 μm | 173.1 μm | 221.7 μm | 119.7 μm | 119.6 μm | toxicity and intravenous administration. CAmB is a lipid-crystal, nano-particle formulation designed for targeted oral delivery of amphotericin B (AmB) to the infected tissue without the associated toxicity.

Sixty-five BALB/c mice were infected on Day 0 with $5 \times 10^5$ cells of *Candida albicans*. Twenty-four hours after infection mice were treated for up to 14 days with control, DAmB 2 mg/kg (intraperitoneal), or CAmB 10 mg/kg (oral). A group of untreated and uninfected mice were used as blank controls. Five mice from each treatment group were sacrificed on days 1, 3, 5, 7, 11, and 15. Plasma and tissues were collected for analysis of AmB concentrations.

Figure 4:
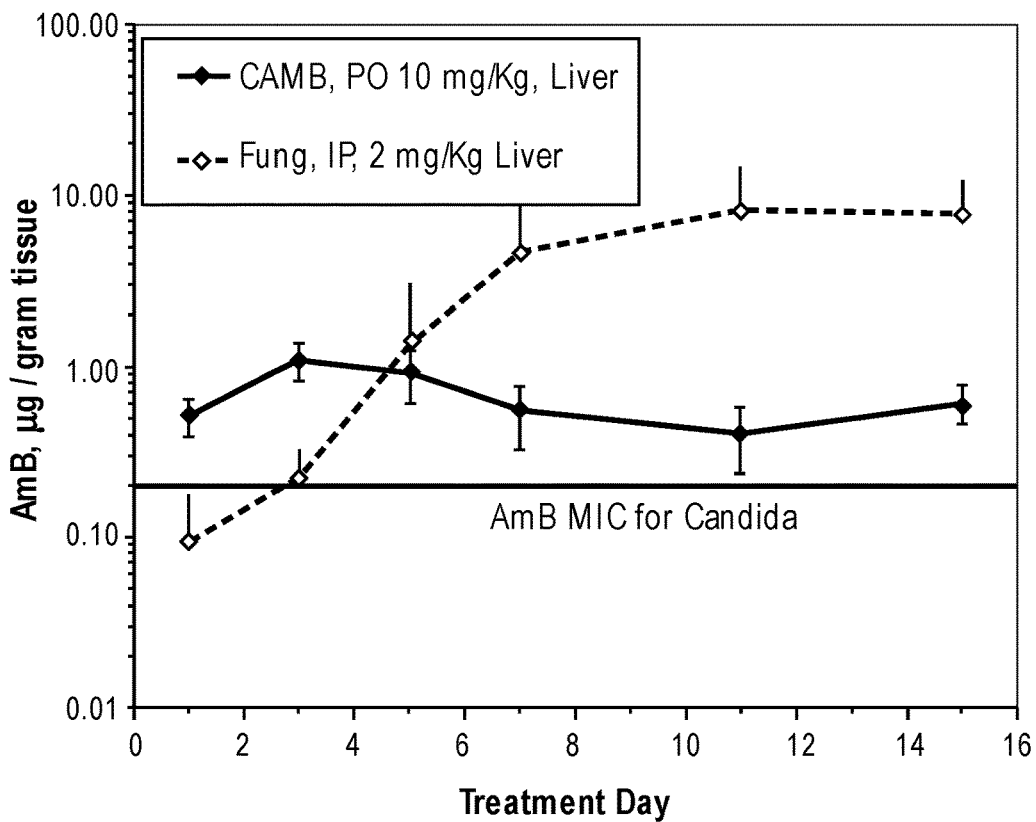
FIG. 4 shows a time course of the concentration of amphotericin B in the liver tissue of mice infected with *Candida albicans* and treated with either 2 mg/kg of the standard of care amphotericin B deoxycholate (also known as Fungizone) administered intraperitoneally or 10 mg/kg of encochleated amphotericin B (CAMB) administered orally.
Figure 5:
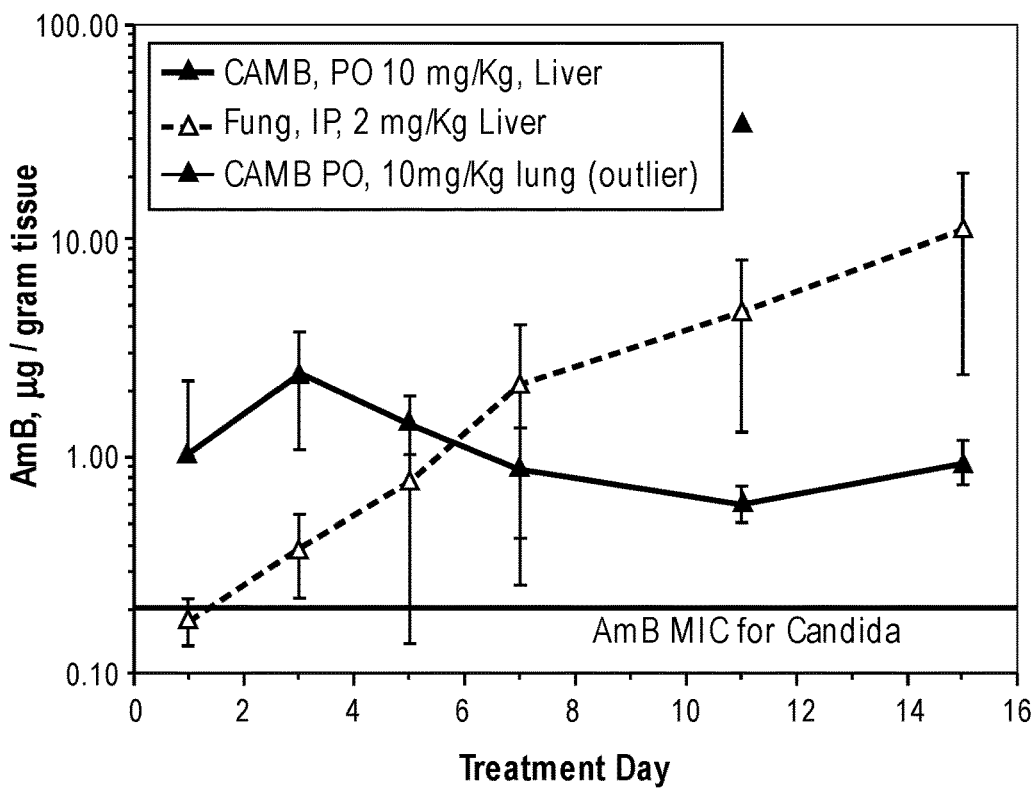
FIG. 5 shows a time course of the concentration of amphotericin B in the lung tissue of mice infected with *Candida albicans* and treated with either 2 mg/kg of the standard of care amphotericin B deoxycholate (also known as Fungizone) administered intraperitoneally or 10 mg/kg of encochleated amphotericin B (CAMB) administered orally.
Figure 6:
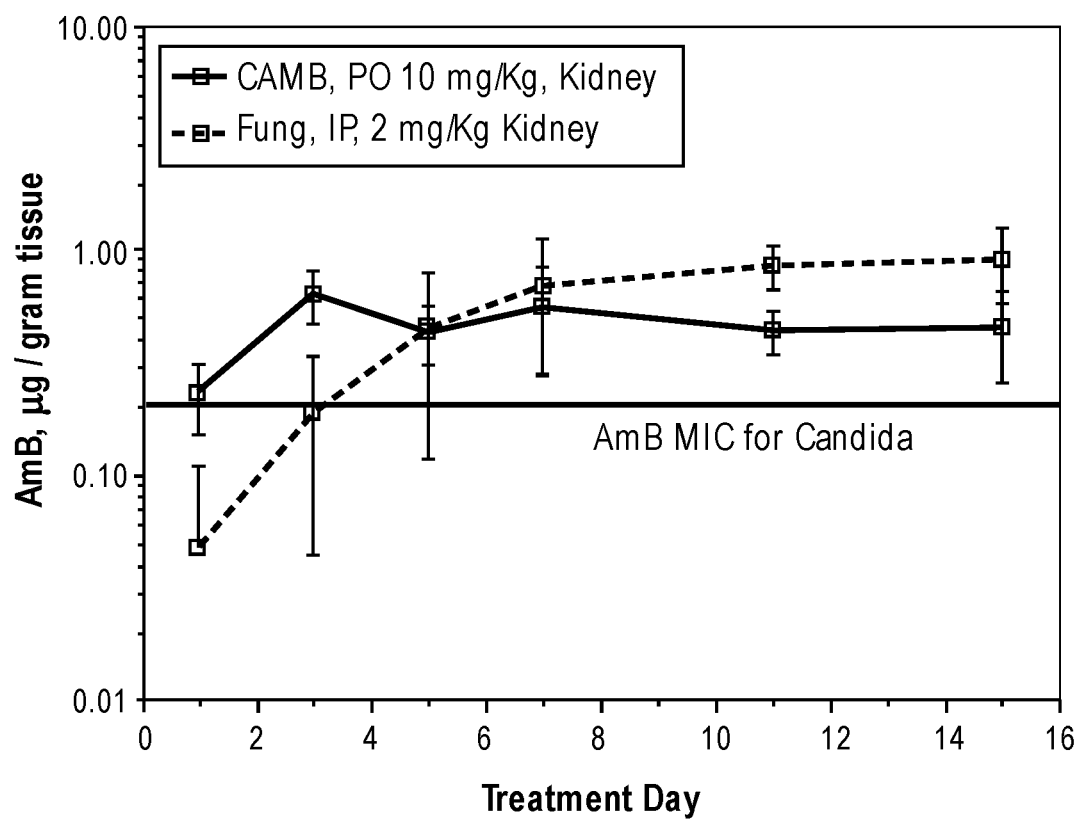
FIG. 6 shows a time course of the concentration of amphotericin B in the kidney tissue of mice infected with *Candida albicans* and treated with either 2 mg/kg of the standard of care amphotericin B deoxycholate (also known as Fungizone) administered intraperitoneally or 10 mg/kg of encochleated amphotericin B (CAMB) administered orally.
Figure 7:
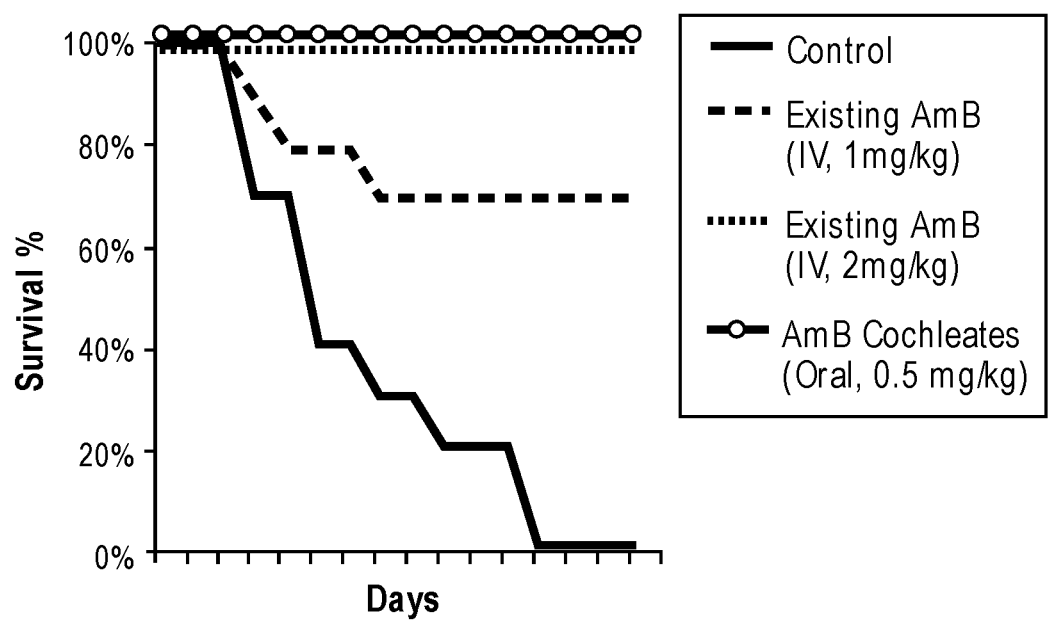
FIG. 7 shows the efficacy of oral administration of 0.5 mg/kg encochleated amphotericin B versus intravenous administration of 2 mg/kg or 1 mg/kg Fungizone ("Existing AmB").

Concentrations of AmB in plasma were undetectable in 61% of the CAmB and 44% of DAmB samples with no significant difference in plasma levels between groups. In the tissues (liver, lung, kidney), however, quantifiable AmB levels were seen in all samples (FIGS. 4-6), with CAmB reaching the minimum inhibitory concentration (MIC) of 0.25 μg/ml within 24 hours whereas DAmB takes 3-5 days to reach the MIC. At the efficacious dose, tissue levels for CAmB stay at 2-3 times the MIC, whereas DAmB causes tissue levels to increase to 4-40 times the MIC during the second week of treatment.

In *Candida*-infected mice, orally administered CAmB is rapidly taken up from the GI tract resulting in tissue concentrations above the MIC level before 24 hours. By contrast, the standard of care, DAmB administered intraperitoneally, takes about 72 hours to reach the MIC. Furthermore, the tissue concentration of AmB following intraperitoneal administration of DAmB continues to rise to levels well above the MIC, even 2 weeks after administration, raising toxicity concerns. In contrast, oral CAmB, after rapidly accumulating in the tissues during the first days of treatment, levels off without escalating to high levels during the second week of treatment, mitigating unwanted side effects and toxicities.

*Candida*-infected mice were also treated with oral, encochleated amphotericin B at a lower dose (0.5 mg/kg) and compared to infected mice administered DAmB intraperitoneally at 1 mg/kg and 2 mg/kg. The encochleated amphotericin B, at a significantly lower dose, exhibited improved efficacy (100% survival rate for duration of study) as compared to DAmB at 1 mg/kg and 2 mg/kg.

Example 5

Comparison of Tissue Levels in Healthy Versus Infected Animals

Toxicology studies of amphotericin B cochleates in healthy Sprague-Dawley rats and dogs were conducted for 28 days, at a range of doses, including 15 mg/kg. Tissue levels (lung, kidney, liver), plasma levels, and urine levels from these rats and dogs at day 28 were determined and compared versus those from the mice treated with amphotericin B cochleates for 14 days in Example 4.

Figure 8:
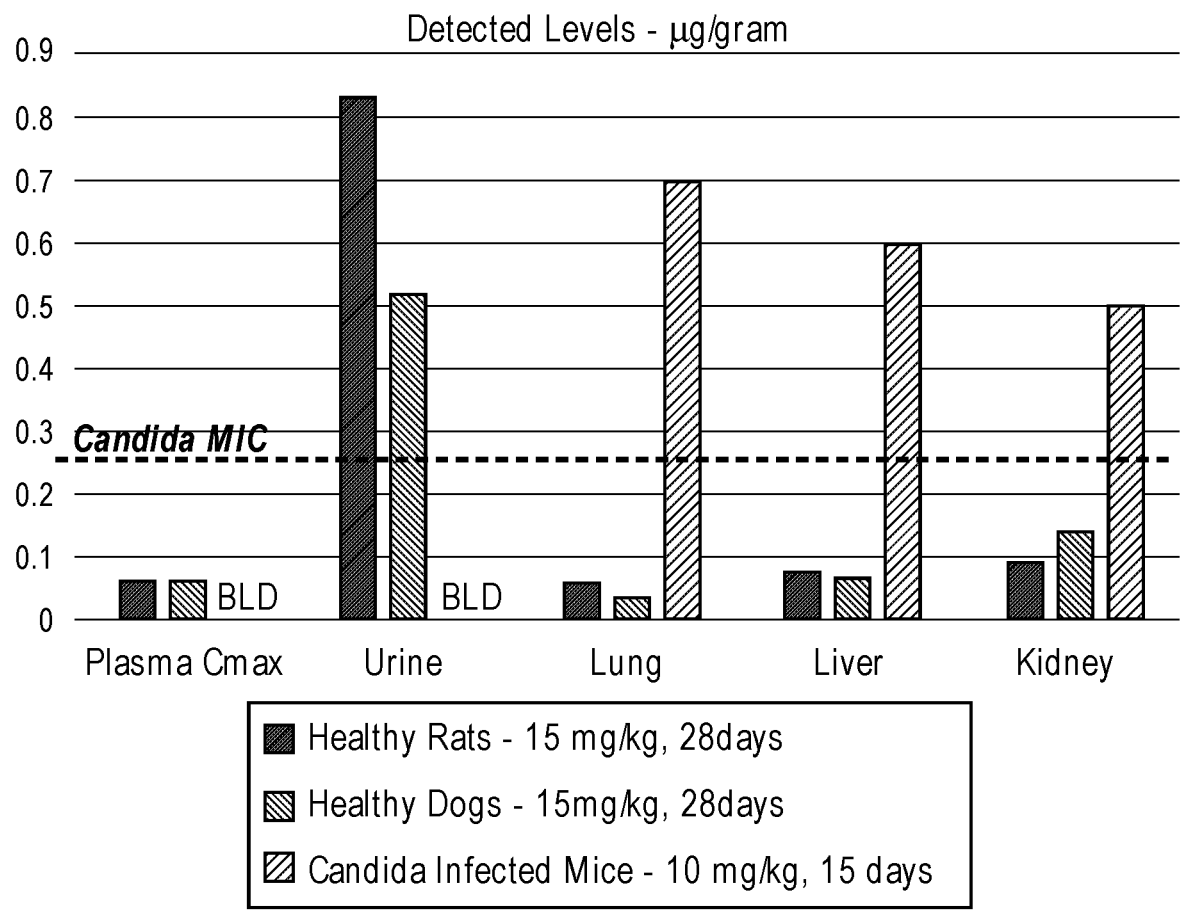
FIG. 8 shows the levels of amphotericin B detected in the plasma, urine, liver, lung, and kidney of healthy animals dosed with amphotericin B cochleates (15 mg/kg) or *Candida*-infected mice treated with amphotericin B cochleates (10 mg/kg). The levels of amphotericin B cochleates were detected at day 28 in the healthy animals and day 15 in the infected animals. BLD indicates below level of detection.

The levels of amphotericin B in lung, liver, and kidney of the infected mice were at least 5-10 times higher (and above MIC levels necessary to treat a *Candida albicans* infection) than amphotericin B levels in these same tissues of the healthy rats and dogs (all well below MIC level for *C.*
*albicans*). FIG. 8. In contrast, the urine and plasma levels for amphotericin B in the infected mice were below detection levels (BLD), while plasma and particularly urine levels were measurable and much higher in the healthy rats and dogs. FIG. 8. Thus, the pharmacokinetics of encochleated drugs, such as amphotericin B, in infected subjects are very different from pharmacokinetics of encochleated drugs, such as amphotericin B, in healthy subjects, with the encochleated drug concentrating at much higher levels in the tissues of infected, but not healthy, animals.

Example 6

Pharmacokinetics and Efficacy of Encochleated Atovaquone (eATQ) in Murine Model of Pneumocystis Atovaquone (ATQ) is an alternative agent for prophylaxis and treatment of pneumocystis pneumonia (PCP) and toxoplasmosis. Small molecule atovaquone suffers clinical limitations of poor patient tolerability, saturable absorption, and nonlinear pharmacokinetics. We prepared ATQ cochleates and studied the biodistribution, pharmacokinetics (PK), and efficacy of encochleated ATQ in immunocompromised mice infected with *Pneumocystis murina*.

Mice were immunocompromised with dexamethasone and infected with *P. murina*. In the PK study, mice were treated with eATQ 100 mg/kg via oral gavage, followed by sacrifice and blood and lung tissue collection at 0 (baseline), 2, 4, 8, 10, 12, 24, 48, 72, and 96 hours post-dose (n=30, 3 at each time point). In the treatment study, mice were treated daily via oral gavage for 7, 14, and 21 days each with one of the following: eATQ 50 mg/kg, eATQ 100 mg/kg, atovaquone suspension 100 mg/kg, sulfamethoxazole/trimethoprim 3/100 mg/kg, or vehicle control (n=138, 8-10 per group). Mice were sacrificed and lungs were processed for microscopic enumeration of pneumocystis asci and nuclei.

Figure 9:
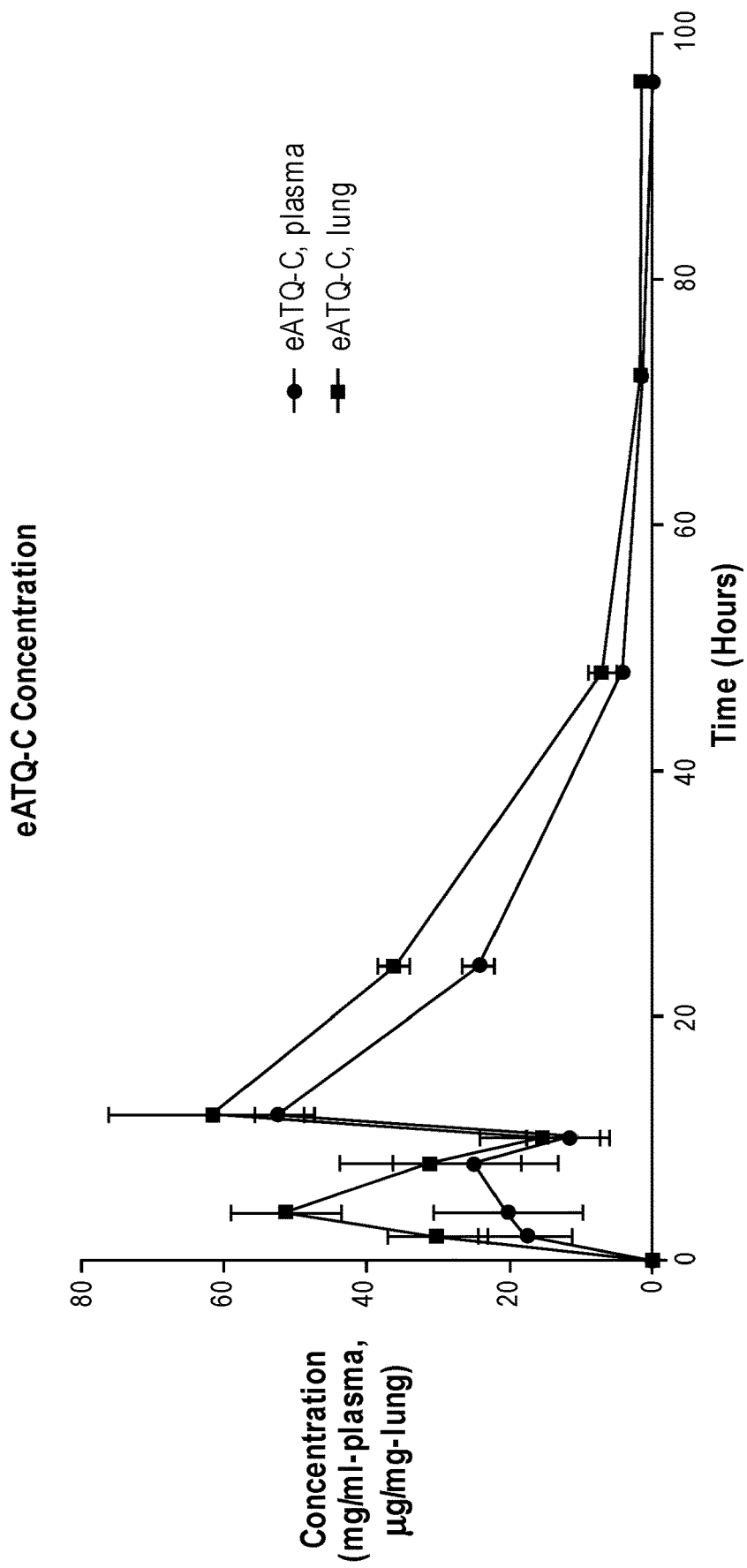
FIG. 9 shows a time course of the concentration of ATQ in the plasma and lungs of mice infected with *P. murina* and treated with encochleated ATQ (eATQ) at a dosage of 100 mg/kg via oral gavage.
Figure 10A:
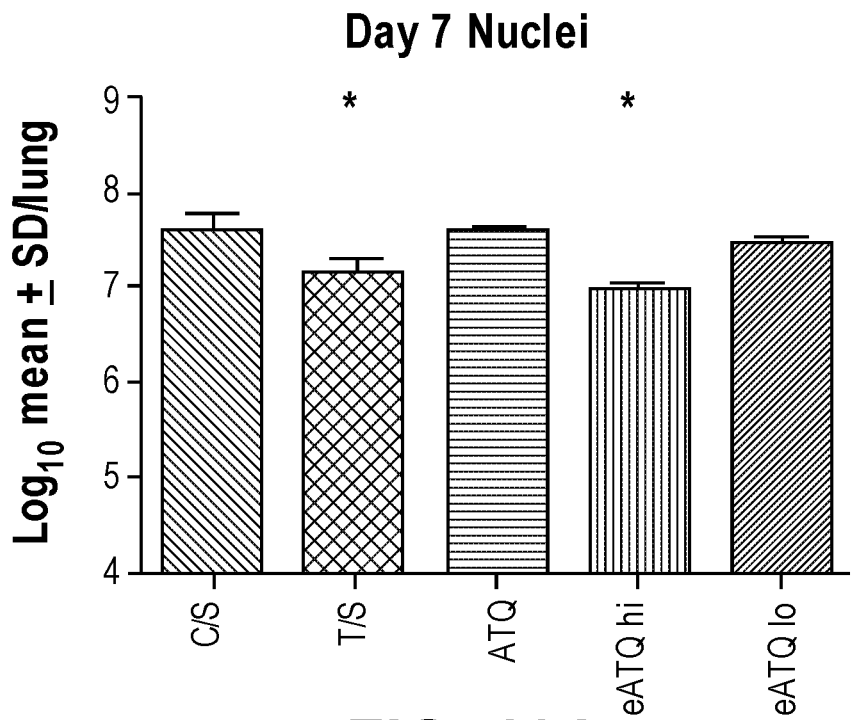
FIGS. 10A-F show the mean nuclei and asci counts after 7 (FIGS. 10A-B), 14 (FIGS. 10C-D), and 21 (FIGS. 10E-F) days in mice infected with *P. murina* and treated with 1) vehicle (cochleate) control without ATQ (C/S), 2) trimethoprim/sulfamethaxozole (T/S), 3) non-encochleated ATQ (ATQ), 4) encochleated ATQ at 100 mg/kg via oral gavage (eATQ hi), or 5) encochleated ATQ 50 mg/kg via oral gavage (eATQ lo).
Figure 10B:
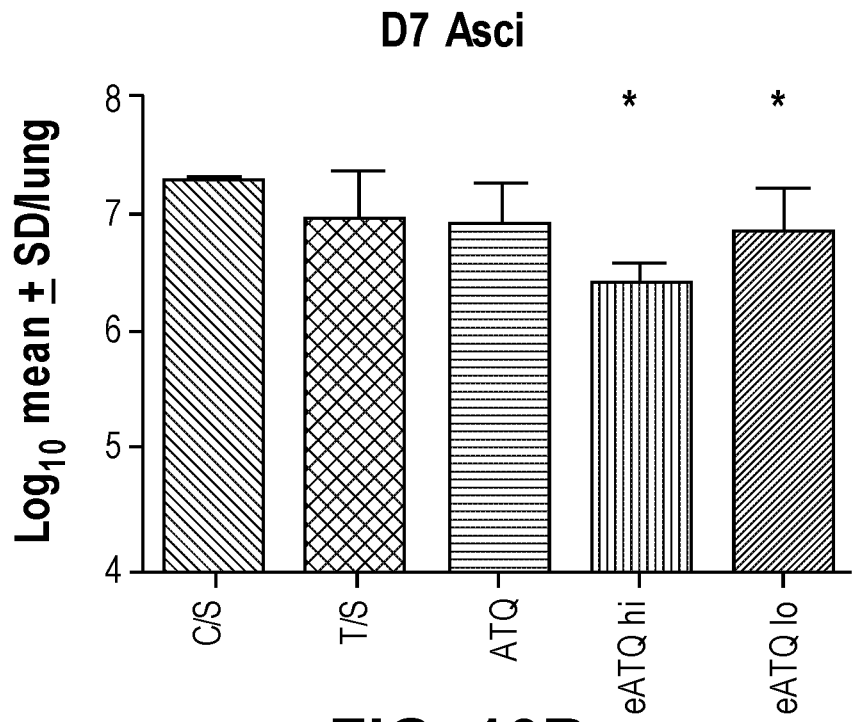
Figure 10C:
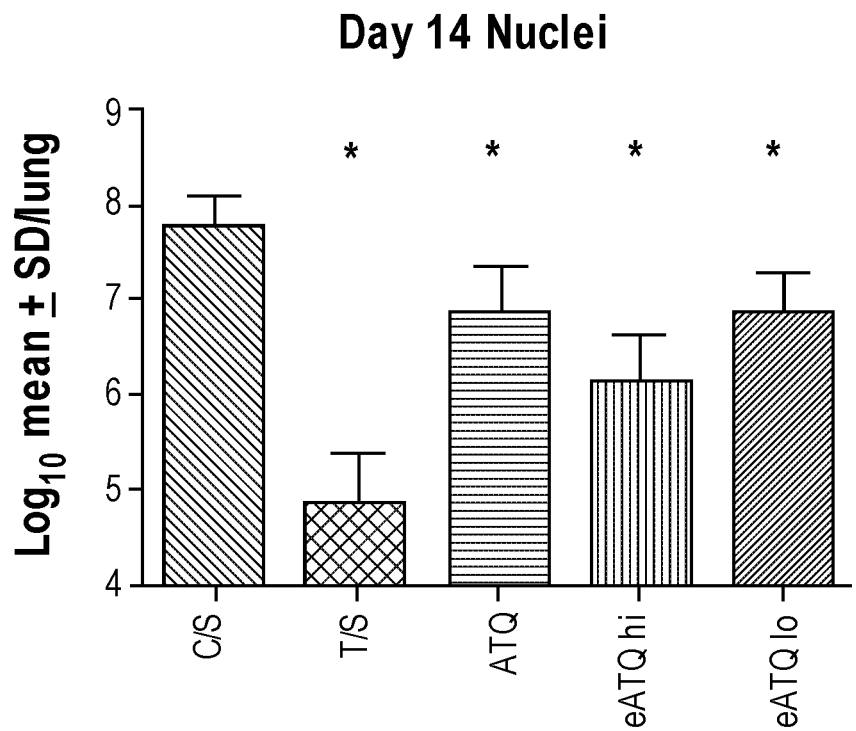
Figure 10D:
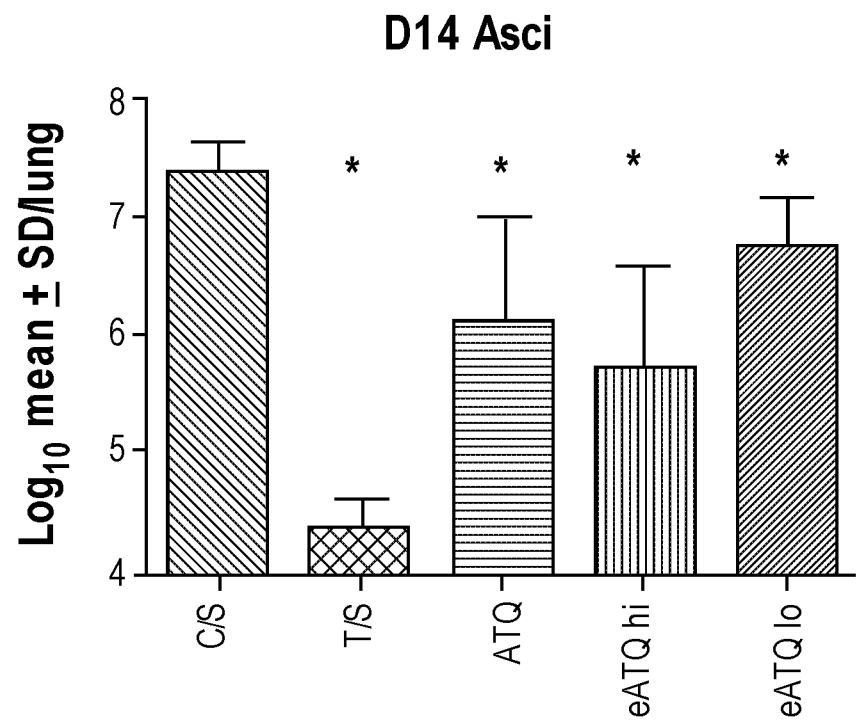
Figure 10E:
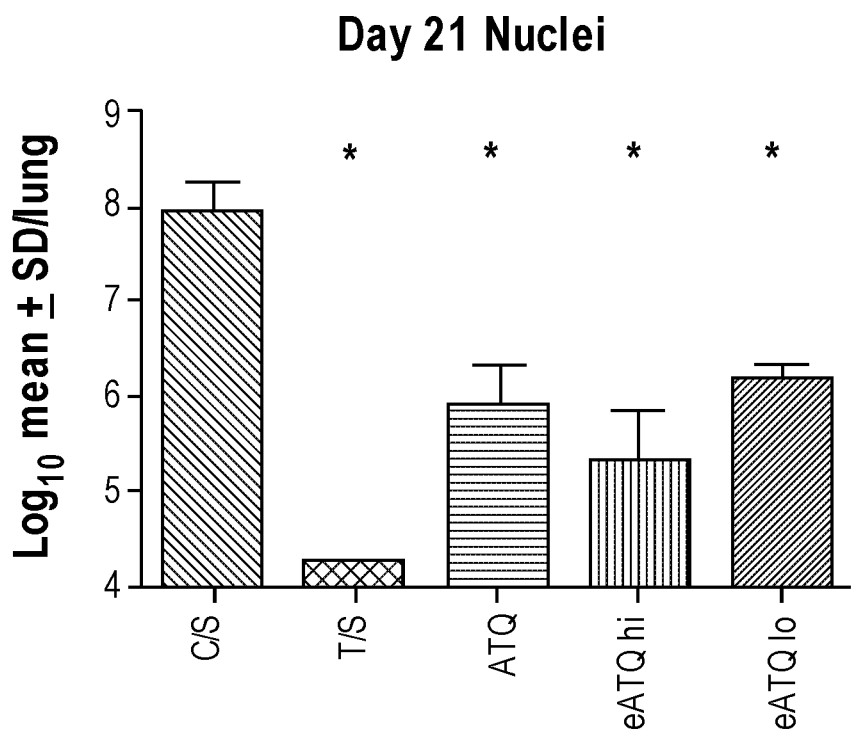
Figure 10F:
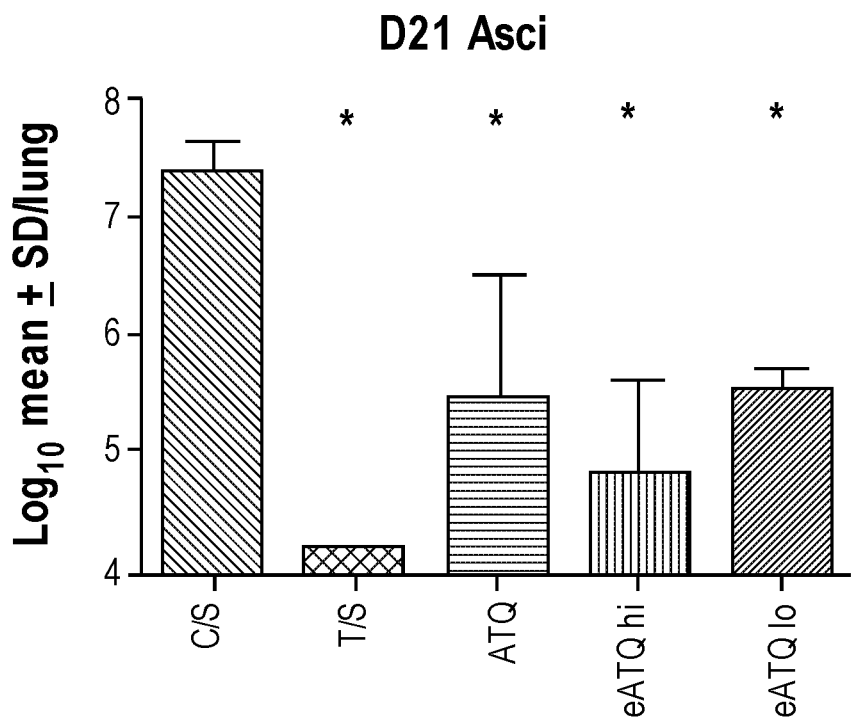
Figure 11A:
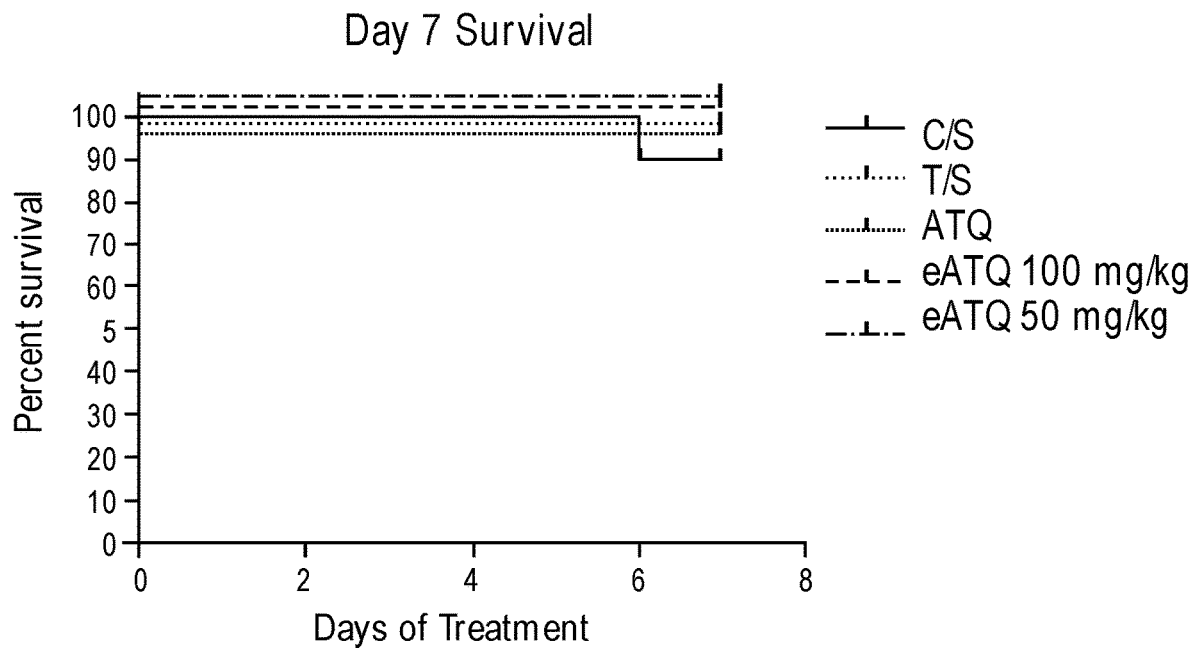
FIGS. 11A-C show the survival curves after 7 (FIG. 11A), 14 (FIG. 11B), and 21 (FIG. 11C) days in mice infected with *P. murina* and treated with 1) vehicle (cochleate) control without ATQ (C/S), 2) trimethoprim/sulfamethaxozole (T/S), 3) non-encochleated ATQ (ATQ), 4) encochleated ATQ at 100 mg/kg via oral gavage, or 5) encochleated ATQ 50 mg/kg via oral gavage.
Figure 11B:
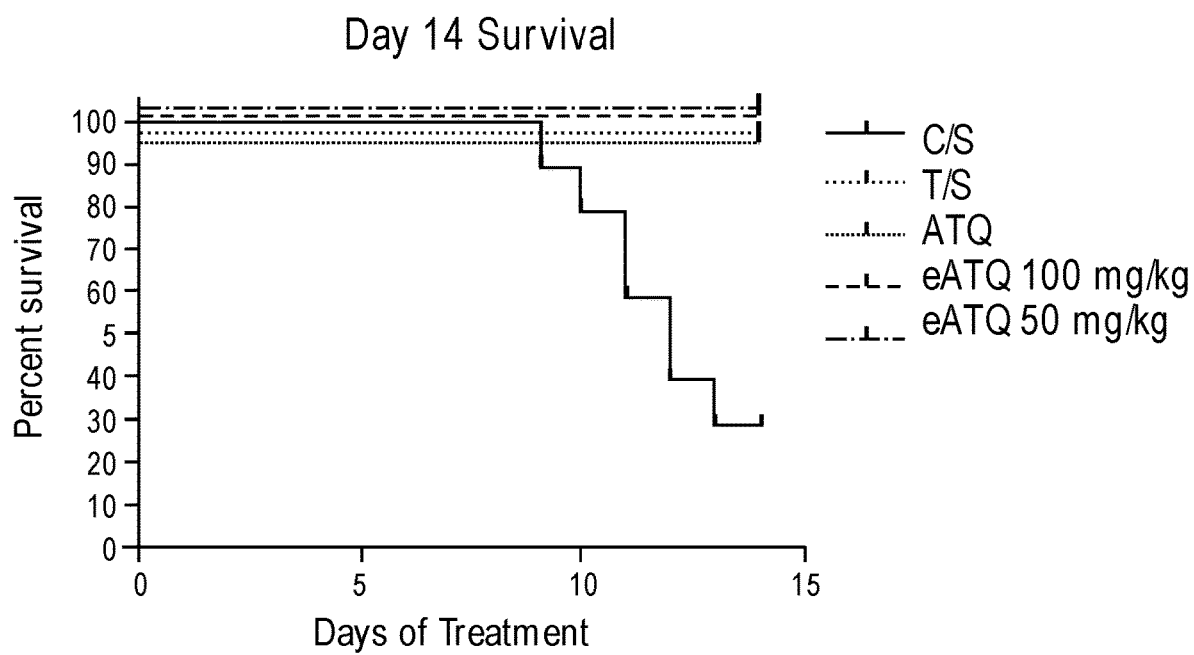
Figure 11C:
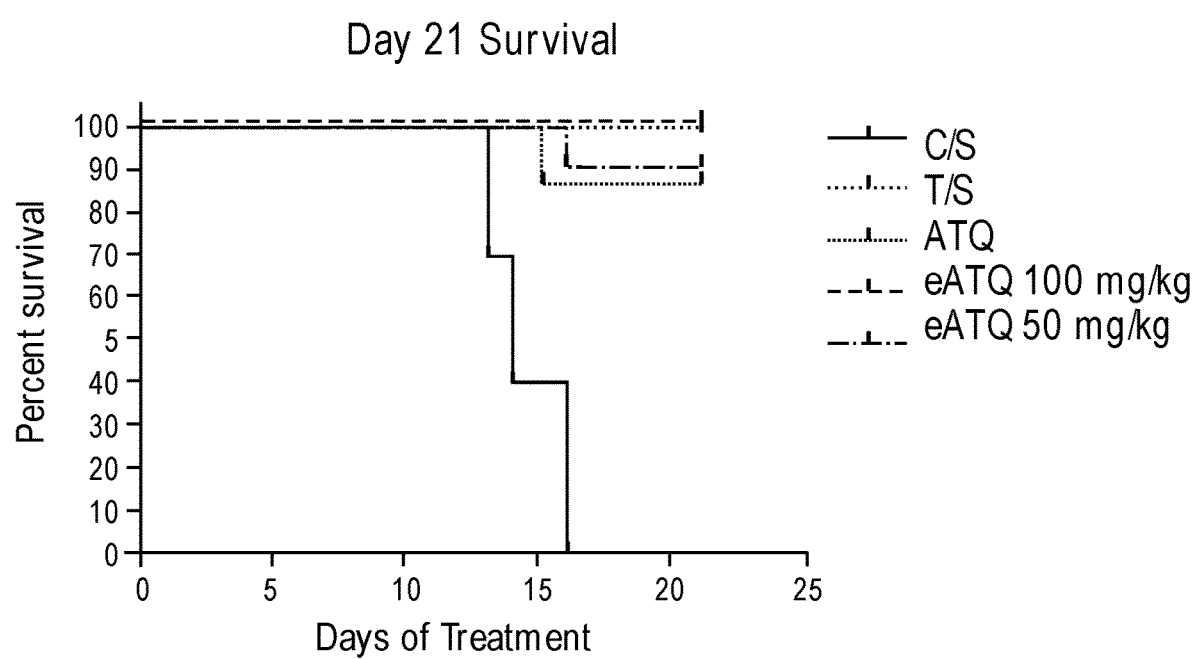

Geometric means of maximal concentrations (Cmax) and area under the curve (AUC) were 18% and 44% higher, respectively in lung than in plasma. FIG. 9. Half life was 10-12 hours in plasma and 15-17 hours in lungs, and Tmax was 12 hour in both. FIG. 9. There was a significant reduction in both nuclei and asci counts in both the 100 mg/kg and 50 mg/kg dose at all three time points versus the vehicle control (C/S) except the day 7 nuclei counts versus C/S in the 50 mg/kg group. FIG. 10A-F. There was a consistent dose response between the two doses at all time points. FIG. 10A-F. All treated groups showed a significant improvement in survival versus the vehicle control (C/S) at the day 14 and 21 time points. FIG. 11A-C. No overt toxicity was observed during the course of the study.

Encochleated ATQ successfully treated PCP in mice and was shown to perform significantly better than the formulation of atovaquone commercially available for the treatment of PCP.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A cochleate composition, the composition comprising a plurality of cochleates comprising at least one negatively charged phospholipid, a multivalent cation, a pharmacologically active agent, and a size-regulating agent selected from the group consisting of a lipid-anchored polynucleotide, a lipid-anchored sugar, and a lipid-anchored polypeptide,
   wherein the lipid-anchored polynucleotide is a polynucleotide covalently bound to a lipid anchor selected from saturated or unsaturated fatty acids having 12 to 38 carbon atoms, sterols, and vitamins,
   wherein the lipid anchor is indirectly linked to the polynucleotide, the sugar, or the polypeptide by a covalently bound spacer consisting of polyethylene glycol.

2. The cochleate composition of claim 1, wherein the mean particle size of the plurality of cochleates is less than 10 microns.

3. The cochleate composition of claim 2, wherein the mean particle size of the plurality of cochleates is less than 1 micron.

4. The cochleate composition of claim 3, wherein the mean particle size of the plurality of cochleates is between 400-800 nm.

5. The cochleate of claim 1, wherein the mean particle size of the plurality of cochleates is 2-3 times smaller than the mean particle size of cochleates made without the size-regulating agent.

6. The cochleate composition of claim 1, wherein the tissue level of the pharmacologically active agent in an infected or an inflamed tissue at 24 hours following oral administration of the cochleate composition to the subject is at least 1.5 times higher than the tissue level of the pharmacologically active agent at 24 hours following oral administration to a healthy subject.

7. The cochleate composition of claim 1, wherein the pharmacologically active agent is selected from the group consisting of an anti-fungal, an anti-bacterial, an anti-viral, an anti-parasitic, anti-protozoal or antihelminthic, a vaccine, an anti-inflammatory agent, a polynucleotide, an immunotherapy, an anti-cancer agent, an anti-dyslipidemia agent, an anti-dementia agent, a nutritional supplement, an herbal product, and a vitamin.

8. The cochleate composition of claim 1, wherein the multivalent cation is a divalent metal cation.

9. The cochleate composition of claim 8, wherein the divalent metal cation is calcium.

10. The cochleate composition of claim 1, wherein the at least one negatively charged phospholipid is present in an amount of about 20%-80% of the total phospholipid content of the cochleate composition.

11. A method of treating a subject in need thereof, the method comprising administering the cochleate composition of claim 1 to the subject.

12. The cochleate composition of claim 7, wherein the anti-bacterial is a beta-lactamase inhibitor.

13. The cochleate composition of claim 8, wherein the divalent metal cation is calcium, zinc, magnesium, or barium.

14. The cochleate composition of claim 7, wherein the polynucleotide is selected from the group consisting of siRNA, iRNA, anti-sense therapy, and gene therapy polynucleotides.

15. The cochleate composition of claim 1, wherein the size-regulating agent is the lipid-anchored polynucleotide.

16. The cochleate composition of claim 1, wherein the size-regulating agent comprises a lipid-anchored sugar or a lipid-anchored polypeptide.

17. The cochleate composition of claim 1, wherein the saturated or unsaturated fatty acid having 12 to 38 carbon atoms is palmitate.

* * * * *